(12) United States Patent
Kim et al.

(10) Patent No.: US 8,237,018 B2
(45) Date of Patent: Aug. 7, 2012

(54) PROMOTES AND METHODS THEREOF

(75) Inventors: Ju-Kon Kim, Seongnam-si (KR); Su-Hyun Park, Yongin-si (KR); Nari Yi, Namyangju-si (KR); Yang-Do Choi, Seocho-gu (KR); Baek-Hie Nahm, Seongnam-si (KR)

(73) Assignee: Myongji University Industry and Academia Cooperation Foundation, Gyeonggi-do (KR)

( * ) Notice: Subject to any disclaimer, the term of this patent is extended or adjusted under 35 U.S.C. 154(b) by 295 days.

(21) Appl. No.: 12/583,623

(22) Filed: Aug. 24, 2009

(65) Prior Publication Data

US 2011/0047648 A1 Feb. 24, 2011

(51) Int. Cl.
*A01H 5/00* (2006.01)
*C12N 15/82* (2006.01)
*C07H 21/04* (2006.01)

(52) U.S. Cl. .................. 800/298; 435/419; 435/320.1; 536/24.1

(58) Field of Classification Search ............... None
See application file for complete search history.

(56) References Cited

U.S. PATENT DOCUMENTS

| 4,940,838 | A | 7/1990 | Schilperoort et al. |
| 6,958,434 | B2 | 10/2005 | Kim et al. |
| 7,365,185 | B2 * | 4/2008 | Boukharov et al. .......... 536/24.1 |

FOREIGN PATENT DOCUMENTS

| EP | 0120516 | 3/1984 |
| EP | 0116718 | 8/1984 |
| EP | 0301316 | 1/1989 |

OTHER PUBLICATIONS

Sequence Accession ACL37128, Kreps et al, Jun. 2, 2005.*
Jang et al.,"Subcellular targeting of green fluorescent protien to plastids in transgenic rice plants provides a high-level expression syste", Molec. Breeding, 1999; 5, 453-61.

* cited by examiner

*Primary Examiner* — Elizabeth McElwain
(74) *Attorney, Agent, or Firm* — IP Legal Services, LLC

(57) ABSTRACT

A promoter, which may be used to transform a plant and/or express a gene substantially uniformly in substantially all organs and/or tissues of a plant, and which may include a constitutive expression promoter for transforming a monocot plant. A vector including a promoter, which may include a recombinant plant expression vector. A method of producing a target protein using a vector, and a method of producing a transformed cell and/or plant using a vector. A transformed plant, a transformed seed and a transformed cell are included, which may be formed by the method of producing the same using a vector. A PCR primer for a promoter is provided.

14 Claims, 7 Drawing Sheets
(3 of 7 Drawing Sheet(s) Filed in Color)

PROMOTES AND METHODS THEREOF

BACKGROUND

The present invention generally relates to promoters and methods of use and fabrication thereof, and particularly to a promoter used to express a gene, a vector including a promoter, a method of producing a target protein, a method of producing a transformed cell and/or a plant, a transformed plant, a transformed seed, a transformed cell, and PCR primers for a promoter.

A promoter may relate to a genomic region located upstream of a structural gene and may function in the transcription of a structural gene, for example, into mRNA. A promoter may be activated by binding of general transcription factors, and may include base sequences such as a TATA box and/or CAT box which may assist to regulate gene expression. For example, promoters linked to genes may be constitutively activated by general transcription factors to express genes associated with proteins needed for the basal metabolism of a living organism and which may be required in cells at a given concentration. Promoters may also be activated when proteins are needed which are not ordinarily present or only required under special circumstances. For example, inducible promoters may be activated by binding of specific transcription factors, which may be activated in an organism's developmental processes or by external stimuli resulting from surrounding environmental factors.

A foreign gene (i.e., transgene) introduced into a plant, forming a plant having novel characteristics which may develop an agricultural field, may be influenced by transcriptional, post-transcriptional, translational and post-translational elements. A promoter may belong to a transcriptional element and may directly influence transcription of a transgene, for example, to change the expression level of a transgene. A promoter may be the most important factor to change the expression stage or the tissue and/or cell specificity of a transgene.

Although promoters have been isolated from plants to express a transgene, only a few promoters may be practical for use in the transformation of plants. For example, a CaMV (cauliflower mosaic virus) 35S promoter and its derivatives may induce expression of genes in plant tissues and exhibit high activity, for example in vascular tissues and root/leave cells. However, a CaMV 35S promoter has relatively less activity in monocot plants, such as a rice plant, and does not exhibit any activity in certain cells, such as pollen.

Promoters from dicot plants which have been investigated for the transformation of monocot plants have exhibited relatively lower activity compared to promoters originating from monocot plants. A rbcS (ribulose bisphosphate carboxylase/oxygenase small subunit) promoter of rice, a Act1 (actin1) promoter of rice, and a Ubi1 promoter of maize are examples of promoters from monocot plants which have been investigated in the transformation of monocot plants. While Act1 and Ubi1 promoters exhibit a relatively high activity in monocot plants compared to a CaMV 35S promoter, there are drawbacks. For example, the Act1 promoter exhibits activity mainly in vegetative tissue and reproductive tissue, and thus is not effective for expression of a ubiquitous gene in monocot plants. Although the Ubi1 promoter exhibits activity in numerous types of cells, it does not exhibit activity in the substantially all tissues of a plant. Also, while the Ubi1 promoter exhibits a strong activity, especially in young roots, the activity is greatly reduced over time, for example as the root grows.

Accordingly, there is a need for developing a promoter exhibiting a strong, stable and ubiquitous activity in the transformation of plants, including monocot plants. There is a need for suitable promoters useful in the substantially uniform expression of a gene in substantially all the tissues of a plant. There is a need for suitable promoters useful in the production of transformed compositions, and suitable methods for fabricating the same. There is also a need for suitable primers for a variety of novel promoters.

SUMMARY

Embodiments relate to a promoter. In example embodiments, a promoter may include at least one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19 and SEQ ID NO: 20 (i.e., SEQ ID NO: 1 through SEQ ID NO: 20).

Embodiments relate to a promoter that may be a constitutive expression promoter and may be configured to transform a plant, such as a monocot plant. In example embodiments, a monocot plant may include at least one of a rice, barley, wheat, maize, millet and Indian millet. In embodiments, a promoter may express a gene substantially uniformly in substantially all organs and/or tissues of a plant.

Embodiments relate to a promoter that may include a base sequence complementary to at least one of SEQ ID NO: 1 through SEQ ID NO: 20. In embodiments, a promoter may include a variant of at least one of SEQ ID NO: 1 through SEQ ID NO: 20. In embodiments, a promoter may include a base sequence complementary to a variant of at least one of SEQ ID NO: 1 through SEQ ID NO: 20.

Embodiments relate to a vector. In example embodiments, a vector may include a promoter comprising at least one of SEQ ID NO: 1 through SEQ ID NO: 20. In embodiments, a vector may be a recombinant plant expression vector and may include a constitutive expression promoter configured to transform a plant, such as a monocot plant. In embodiments, a target gene downstream of a promoter encoding a target protein may be operably linked. In embodiments, a promoter of a vector may expresses a gene substantially uniformly in substantially all organs and/or tissues of a plant. In embodiments, a vector may include a variant of at least one of SEQ ID NO: 1 through SEQ ID NO: 20.

Embodiments relate to a transformed plant. In example embodiments, a plant may include a promoter comprising at least one of SEQ ID NO: 1 through SEQ ID NO: 20. Embodiments relate to a transformed seed. In example embodiments, a seed may include a promoter comprising at least one of SEQ ID NO: 1 through SEQ ID NO: 20. Embodiments relate to a transformed cell. In example embodiments, a cell may include a promoter comprising at least one of SEQ ID NO: 1 through SEQ ID NO: 20.

Embodiments relate to a method of forming a target protein. In embodiments, a plant may be transformed using a vector that may include a promoter which may include at least one of SEQ ID NO: 1 through SEQ ID NO: 20. In example embodiments, a target protein may include at least one of interleukin, interferon, platelet-derived growth factor, hemoglobin, elastin, collagen, insulin, fibroblast growth factor, human growth factor, human serum albumin and erythropoietin.

Embodiments relate to a method of transforming a cell and/or plant. In embodiments, a plant cell may be transformed using a vector that may include a promoter which may include at least one of SEQ ID NO: 1 through SEQ ID NO: 20. In example embodiments, a transformed plant may be redifferentiated from a transformed plant cell.

Embodiments relate to a PCR primer. In embodiments, a primer may include at least one of SEQ ID NO: 67 through SEQ ID NO: 106. In example embodiments, a primer may react with a promoter including at least one of SEQ ID NO: 1 through SEQ ID NO: 20. Embodiments relate to a primer including a base sequence complementary to at least one of SEQ ID NO: 67 through SEQ ID NO: 106. Embodiments relate to a primer including a variant of at least one of SEQ ID NO: 67 through SEQ ID NO: 106. Embodiments relate to a base sequence complementary to the variant at least one of SEQ ID NO: 67 through SEQ ID NO: 106.

DRAWINGS

The patent or application file contains at least one drawing executed in color. Copies of this patent or patent application publication with color drawing(s) will be provided by the Office upon request and payment of the necessary fee.

DESCRIPTION

Figure 1:
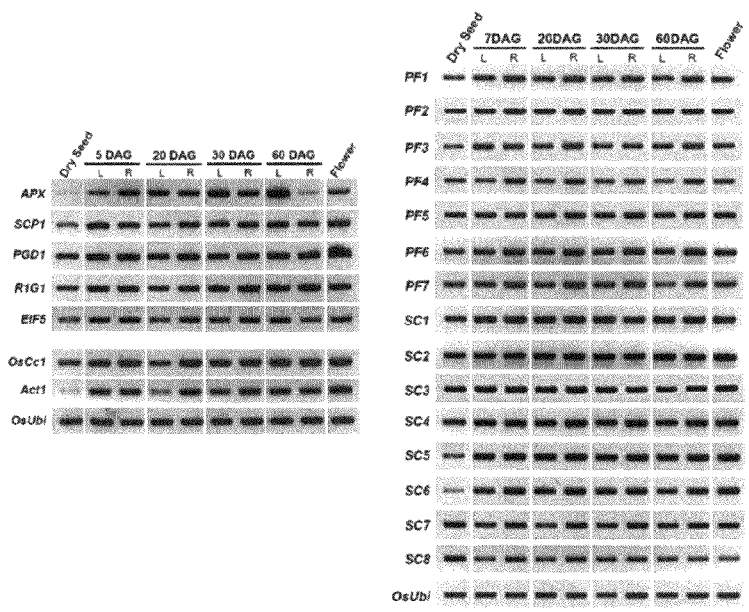
FIG. 1 shows the expression of genes according to embodiments relative to related promoters (OsCc1, Act1 and Ub1) in various tissues of a plant.

Embodiments relate to a promoter derived from monocot plants, such as rice. In embodiments, the promoter may be suitable for the transformation of plants including monocot plants and may be suitable for the constitutive expression of plant genes. A promoter according to embodiments may express a gene substantially uniformly in substantially all the organs and/or tissues of a plant. In embodiments, a promoter may include at least one of SEQ ID NO: 1 through SEQ ID NO: 20 and may include base sequences complementary to the base sequences of SEQ ID NO: 1 to SEQ ID NO: 20. "Complementary" may relate to hybridization and/or base pairing between nucleotides or nucleic acids, for instance, between two strands of a DNA molecule.

A promoter may relate to a DNA molecule to which RNA polymerase binds in order to initiate transcription and may refer to a DNA region upstream of a structural gene. A plant promoter may relate to a promoter which may initiate transcription in a plant cell. A constitutive promoter may relate to a promoter which may be active in most environmental conditions and/or development states and/or cell differentiation states. Since the selection of a transformant may be carried out by various tissues at various stages, a constitutive promoter may be preferable. However, one is not limited to selecting a constitutive promoter according to embodiments.

In embodiments, a promoter may include at least one of an ascorbate peroxidase (APX) promoter of SEQ ID NO: 1, an AP2 domain containing putative gene (SCP1) promoter of SEQ ID NO: 2, a cytosolic phosphogluconate dehydrogenase (PGD1) promoter of SEQ ID NO: 3, a putative R1G1 domain containing protein (R1G1) promoter of SEQ ID NO: 4, a translation initiation factor EIF-5A (EIF5) promoter of SEQ ID NO: 5, a PF1 promoter (60S acidic ribosomal protein P1) of SEQ ID NO: 6, a PF2 promoter (translationally controlled tumor protein) of SEQ ID NO: 7, a PF3 promoter (probable aquaporin of SEQ ID NO: 8, a PF4 promoter (40S ribosomal protein S8) of SEQ ID NO: 9, a PF5 promoter (ubiquitin-conjugating enzyme OsUBC5b) of SEQ ID NO: 10, a PF6 promoter (ribosomal protein S26E family protein of SEQ ID NO: 11, a PF7 promoter (60S ribosomal protein L18) of SEQ ID NO: 12, an SC1 promoter (peptidyl-prolyl cis-trans isomerase) of SEQ ID NO: 13, an SC2 promoter (histone H3.3) of SEQ ID NO: 14, an SC3 promoter (glyceraldehyde-3-phosphate dehydrogenase) of SEQ ID NO: 15, an SC4 promoter (heat shock protein 82) of SEQ ID NO: 16, an SC5 promoter (60S ribosomal protein L9) of SEQ ID NO: 17, an SC6 promoter (plectin S10) of SEQ ID NO: 18, an SC7 promoter (histone H2B.1) of SEQ ID NO: 19, and an SC8 promoter (histone H2B.1) of SEQ ID NO: 20.

In embodiments, a promoter may include at least one of SEQ ID NO: 1 through SEQ ID NO: 20 and may be configured to transform a plant, including a monocot plant. In embodiments, a monocot plant may be, but is not limited to, at least one of a rice, barley, wheat, maize, millet and Indian millet. In embodiments, a promoter may express a gene substantially uniformly in substantially all the organs and/or tissues of a plant, including a monocot plant.

Embodiments relate to variants of a promoter which may include a variant of at least one of SEQ ID NO: 1 through SEQ ID NO: 20. In embodiments, a variant may have different base sequences but include functional characteristics similar to those of at least one of SEQ ID NO: 1 through SEQ ID NO: 20. A variant may result from at least one of a substitution, deletion and insertion of nucleic acid base(s), or combinations thereof, including functional fragments thereof. In example embodiments, a base sequence complementary to the variant at least one of SEQ ID NO: 1 through SEQ ID NO: 20 may be included.

In example embodiments, a variant of a promoter may have a sequence identity of at least 70%, preferably at least 80%, even more preferably 90%, and most preferably at least 95% to the at least one of SEQ ID NO: 1 through SEQ ID NO: 20. A percentage of sequence identity to a polynucleotide may be determined by comparing two optimally aligned sequences over a comparison window, wherein the portion of the polynucleotide sequence in the comparison window may include additions or deletions (i.e., gaps) and/or substitutions as compared to the reference sequence (which does not include additions, deletions or substitutions) for optimal alignment of the two sequences.

Substantial identity of polynucleotide sequences may relate to a polynucleotide including a sequence having between 50-100% sequence identity, preferably at least 70% sequence identity, preferably at least 80% sequence identity, more preferably at least 90%, and most preferably at least 95%. Substantial identity may also relate to when two nucleotide molecules are hybridized specifically to each other under a stringent condition such that their sequences may be substantially identical to each other. For example, stringent condition may vary depending on nucleotide sequences, and thus can be different at a different condition. At certain ionic strength and pH, for example, a stringent condition may be selected to have a temperature that is about 10° C. lower than the heat-melting point (Tm) of a specific sequence. Tm may relate to a temperature at which 50% of a target sequence is hybridized to a fully complementary probe (under the condition of certain ionic strength and pH). For example, a stringent condition for carrying out Southern blot analysis may include washing with 0.2×SSC at 65° C. For an oligonucleotide probe, washing may be carried out with 6×SSC at 42° C.

Embodiments relate to a vector. A vector may relate to a DNA fragment(s) and/or nucleotide molecules delivered to a cell. A vector may replicate DNA and be independently reproduced in a host cell. The terms "delivery system" and "vector" may be interchangeably used. An expression vector may relate to a recombinant DNA molecule including a desired coding sequence and other appropriate nucleotide sequences that are essential for the expression of a coding sequence in a specific host organism, such an operatively-linked coding sequence. The aforementioned other appropriate sequences may include at least one of an promoter, an enhancer, a termination signal and a polyadenylation signal that may be suitable for use in a eukaryotic cell. For example, any related terminator may be used according to embodiments. Examples thereof include, but are not limited to, nopaline synthase (NOS), rice α-amylase RAmyl A terminator, phaseoline terminator, and a terminator for optopine gene of *Agrobacterium tumefaciens*. Since a terminator region may increase the reliability and efficiency of transcription in plant cells, a terminator may be highly preferable.

"Recombinant" may relate to a cell which replicates a heterogeneous nucleotide and/or expresses the nucleotide, a peptide, a heterogeneous peptide, or a protein encoded by a heterogeneous nucleotide. A recombinant cell may express a gene or a gene fragment in a sense or antisense form, which are not found in the natural state of the cell. Embodiments relate to a vector which may be a recombinant vector.

Embodiments relating to vectors which may be used to introduce DNA into a plant host may include viral vectors, for example, non-integrative plant viral vectors, such as derivable from the double stranded plant viruses (for example, CaMV) and single stranded viruses, gemini viruses and the like. The use of such vectors may be preferable, particularly when it is difficult to stably transform a plant host.

Embodiments relating to vectors may preferably include at least one selective marker. A selective marker may relate to a nucleotide sequence having a property which allows selection based on a common chemical method. It may be any kind of gene that may be used for the differentiation of transformed cells from non-transformed cell. Examples thereof include, but are not limited to, herbicide-resistant genes, such as glyphosate or phosphintricin, and antibiotic-resistant genes, such as kanamycin, G418, bleomycin, hygromycin or chloramphenicol.

In example embodiments, a recombinant plant expression vector may include a Ti-plasmid vector that, when present in a suitable host, such as *Agrobacterium tumefaciens*, is capable of transferring part of itself, the so-called T-region, to a plant cell. Embodiments include different types of Ti-plasmid vectors, for example those disclosed in EP 0 116 718, to transfer chimeric DNA sequences into plant cells, or protoplasts, from which new plants may be generated which stably incorporate said chimeric DNA in their genomes. Particularly preferred forms of Ti-plasmid vectors are the so-called binary vectors as described in EP No. 0 120 516 B1 and U.S. Pat. No. 4,940,838.

In embodiments, a vector may be a recombinant plant expression vector including a promoter in accordance with embodiments. An example of the recombinant plant expression vector may be, but is not limited to, a vector shown in FIG. 2. As shown in the example embodiment of FIG. 2, a modified green fluorescent protein (GFP), a protease inhibitor II terminator gene ($T_{PINII}$), an OsCc1 promoter (Pcytc), a herbicide-resistant gene Bar (phosphinotricine acetyltransferase gene) and a nopaline synthase terminator ($T_{NOS}$) may be operably linked to a promoter according to embodiments. Also as shown in the example embodiment of FIG. 2, a MAR sequence may be attached to the terminal of the right-border sequence. In embodiments, the aforementioned attachment may minimize the change in expression in the chromosome in various sites of the chromosome such that only the inherent activity of the promoter according to embodiments can be measured.

In embodiments a vector, such as recombinant plant expression vector, may be prepared by operably linking a target gene encoding a target protein downstream of a promoter according to embodiments. "Operably linked" may relate to the element of an expression cassette which functions as a unit to express, for example, a heterogeneous protein. In example embodiments, a promoter that may be operably linked to a heterogeneous DNA which may encode a protein may promote the production of functional mRNA corresponding to the heterogeneous DNA.

In embodiments, a target protein may be any kind of protein, and examples thereof include, but are not limited to, proteins having medical utility, such as enzymes, hormones, antibodies or cytokines, and proteins which can accumulate large amounts of nutrients capable of improving the health of animals including humans. Example embodiments of a target protein include, but are not limited to, interleukin, interferon, platelet-derived growth factor, hemoglobin, elastin, collagen, insulin, fibroblast growth factor, human growth factor, human serum albumin and erythropoietin.

Embodiments relate to a method of producing a target protein. In embodiments, the target protein may be produced by transforming a plant using a vector including a promoter in accordance with embodiments. In example embodiments, the target protein may be produced by constitutive expression in a plant and may include transforming a plant with a recombinant plant expression vector. Embodiments of a target protein are described hereinabove.

According to embodiments, plant transformation may refer to any method of introducing DNA is into a plant. Such transformation methods do not necessarily have a period for regeneration and/or tissue culture. In embodiments, transformation of a plant species is possible for dicot plants and for monocot plants. In embodiments, any transformation method can be used to introduce a hybrid DNA according to embodiments to a suitable ancestor cells. Example methods include a calcium/polyethylene glycol method for protoplast transformation, electroporation of protoplasts, microinjection into plant material, (DNA or RNA-coated) particle bombardment of various plant materials, gene gun methods, infection with (non-integrative) viruses, in planta *Agrobacterium tumefaciens*-mediated gene transfer by infiltration of adult plants or transformation of mature pollen or microspores (EP 0 301 316) and the like. A preferred method according to embodiments may include *Agrobacterium*-mediated DNA transfer. More preferably, use of a so-called binary vector technology, disclosed in EP A 120 516 and U.S. Pat. No. 4,940,838, may be used.

According to embodiments, a plant cell that may be used in plant transformation may be any plant cell. A plant cell may be a cultured cell, a cultured tissue, a cultured organ or a whole plant, and may preferably be a cultured cell, a cultured tissue or a cultured organ, and most preferably a cultured cell according to embodiments. Plant tissue may relate to a differentiated or undifferentiated plant tissue. Embodiments of a plant tissue include, but are not limited to, root, stem, leaf, pollen, seed, cancerous tissue, and cells of various shapes that are used in culture, namely, single cells, protoplasts, buds and callus tissues. In embodiments, a plant tissue may be in planta or in organ culture, tissue culture or cell culture.

Embodiments relate to a method of producing a transformed cell and/or plant. In embodiments, the method may include transforming a plant cell with a vector including a promoter according to embodiments, and may include differentiating a transformed plant from a transformed plant cell. In example embodiments, a recombinant plant expression vector may be used. In example embodiments, the plant transformation may be mediated by, for example, *Agrobacterium tumefaciens*. In example embodiments, redifferentiation of the transformed plant from the transformed plant cell may be carried out using any related method in the art.

Embodiments relate to a transformed plant, which may be produced by the above-described method. The plant may preferably be, but is not limited to, a monocot plant, and more preferably may be rice, barley, wheat, maize, millet or Indian millet. Embodiments relate to a transformed seed. In embodiments, the transformed seed may be obtained from a transformed plant. A seed preferably may be derived from, but is not limited to, a monocot plant, and more preferably may be from rice, barley, wheat, maize, millet or Indian millet. Embodiments relate to a transformed cell. In embodiments, the transformed cell may be obtained from a transformed plant. A cell preferably may be derived from, but is not limited to, a monocot plant, and more preferably may be from rice, barley, wheat, maize, millet or Indian millet.

Embodiments relate to PCR primers. In embodiments, the primer may include SEQ ID NOS: 67 to 106. In embodiments, the primer may be for a constitutive expression promoter which may be configured to transform a plant, such as a monocot plant. In example embodiments, a promoter may react with at least one of SEQ ID NO: 1 through SEQ ID NO: 20. In example embodiments, a promoter may include a complementary base sequence to the at least one SEQ ID NO: 67 through SEQ ID NO: 106.

Embodiments relate to variants of a primer which may include a variant of at least one of SEQ ID NO: 67 through SEQ ID NO: 106. In embodiments, a variant primer may have different base sequences but include functional characteristics similar to those of at least one of SEQ ID NO: 67 through SEQ ID NO: 106. A variant may result from at least one of a substitution, deletion and insertion of nucleic acid base(s), or combinations thereof, including functional fragments thereof. In example embodiments, a variant of a primer may have a sequence identity of at least 70%, preferably at least 80%, even more preferably 90%, and most preferably at least 95% to the at least one of SEQ ID NO: 67 through SEQ ID NO: 106. In example embodiments, a primer may include a base sequence complementary to the variant at least one of SEQ ID NO: 67 through SEQ ID NO: 106.

Hereinafter, the present invention will be described in further detail with reference to example embodiments. It is to be understood, however, that these examples are for illustrative purposes only and are not to be construed to limit the scope of the present invention.

1. Embodiment of Selection and Extraction of Promoter Sequences

Using the rice genome sequences of the international rice genome sequencing project (IRGSP), which was established in 1997 and completed the sequencing of the rice genome in December, 2004, and gene annotation data from the Institute for Genomic Research (TIGR) which carried out gene annotation based on the rice genome sequences, a region was selected to investigate its activity in a transformation, for example its activity in a vector. An annotated bacterial artificial chromosome (BAC) was selected, and about 2 kbp of sequence upstream from a ATG start codon of a coding sequence (CDS) was selected to be investigated as a promoter region. Only the 2-kbp sequence was extracted, separately, and used as a template for constructing PCR primers for isolating about 1.7-2-kb promoters from the 2-kbp sequence.

2. Embodiment of Analysis of a Constitutive Expression Gene by RT-PCR

For the analysis of a constitutive expression gene, samples were collected from seeds and leaf, root and flower tissues of 5-day-old (or 7-day-old), 20-day-old, 30-day-old and 60-day-old seedlings. For the preparation of the samples, the seeds were disinfected with about 70% ethanol and about 20% chlorax solutions, grown in a dark condition for about 5 days, and then developed in a greenhouse. To extract the total RNA, an RNeasy plant mini-kit (Qiagen, Cat. No. 74904) was used. A first-strand cDNA was synthesized using about 400 ng of the extracted total RNA (Invitrogen, Cat. No. 18080-051), and PCR was performed using about 1 μl of the synthesized cDNA product as a template. The primers used in the PCR reaction were as follows, and an ubiquitin (Ubi) primer set was used as a cDNA loading control.

```
Forward primer APX:
5'- GACCTCTAGACCGCCGTATT-3'    (SEQ ID NO: 21)

Reverse primer APX:
5'- GCCAACCACTCGCAATCCAA-3'    (SEQ ID NO: 22)

Forward primer SCP1:
5'- TCGCTGCCTACGCCAACATC-3'    (SEQ ID NO: 23)

Reverse primer SCP1:
5'- TCGCCGAACTAGCAGGTGAG-3'    (SEQ ID NO: 24)

Forward primer PGD1:
5'- CCGTGAGCTAGCGAGGATCT-3'    (SEQ ID NO: 25)

Reverse primer PGD1:
5'- CCGGTAGGAGTCGAAGTACG-3'    (SEQ ID NO: 26)

Forward primer R1G1:
5'- CTTCTCGATTGCCGTGTGCT-3'    (SEQ ID NO: 27)

Reverse primer R1G1:
5'- GCAAGTCTCAAGCTCTCAAT-3'    (SEQ ID NO: 28)

Forward primer EIF5:
5'- GATCTGCGCTCTGAAGGATA-3'    (SEQ ID NO: 29)
```

```
Reverse primer EIF5:
5'- AACCGCAAGATGGAACAACG-3'      (SEQ ID NO: 30)

Forward primer PF1:
5'- GGTCTCTTCGCCAAGCTCCT-3'      (SEQ ID NO: 31)

Reverse primer PF1:
5'- CGCCTCCTCCTTCTTCTCCT-3'      (SEQ ID NO: 32)

Forward primer PF2:
5'- AGCTCAAGGACCTTCAGTTC-3'      (SEQ ID NO: 33)

Reverse primer PF2:
5'- ACGGCGGACTGCATAGATAA-3'      (SEQ ID NO: 34)

Forward primer PF3:
5'- GGTCACTCCATCGTCAGAAT-3'      (SEQ ID NO: 35)

Reverse primer PF3:
5'- ACTTGCTCCACACTGATCAC-3'      (SEQ ID NO: 36)

Forward primer PF4:
5'- CAATGTGGCAGAGCTGATGG-3'      (SEQ ID NO: 37)

Reverse primer PF4:
5'- GGTCTGTAGGCACGACATAG-3'      (SEQ ID NO: 38)

Forward primer PF5:
5'- GGAGTCCTGCACTTACCATA-3'      (SEQ ID NO: 39)

Reverse primer PF5:
5'- CCATGGCGTACTTCTGTGTC-3'      (SEQ ID NO: 40)

Forward primer PF6:
5'- GAAGCTGTACGCCAAGGT-3'        (SEQ ID NO: 41)

Reverse primer PF6:
5'- TAGGTGCGAGCAACATTAGG-3'      (SEQ ID NO: 42)

Forward primer PF7:
5'- CACAGCCACACGAAGCCATA-3'      (SEQ ID NO: 43)

Reverse primer PF7:
5'- GCACAATGCCGATCGCAACA-3'      (SEQ ID NO: 44)

Forward primer SC1:
5'- AGCACCTTCCACCGCGTGAT-3'      (SEQ ID NO: 45)

Reverse primer SC1:
5'- TTCGCCATGGACAGGATGCC-3'      (SEQ ID NO: 46)

Forward primer SC2:
5'- CTGCGGAGGCATACCTTGTT-3'      (SEQ ID NO: 47)

Reverse primer SC2:
5'- ACACTACGACGCATGCTTCA-3'      (SEQ ID NO: 48)

Forward primer SC3:
5'- AACGTGGACGGTGTTCATCA-3'      (SEQ ID NO: 49)

Reverse primer SC3:
5'- CAACTGCACTGGACGGCTTA-3'      (SEQ ID NO: 50)

Forward primer SC4:
5'- AACACCTTCGGCACCAGGAT-3'      (SEQ ID NO: 51)

Reverse primer SC4:
5'- AAGCGAACAGCAGCAGTCAG-3'      (SEQ ID NO: 52)

Forward primer SC5:
5'- CATCTTGCGGTCGGAGAA-3'        SEQ ID NO: 53)

Reverse primer SC5:
5'- TACGCATCCTCTGTGATGGT-3'      (SEQ ID NO: 54)

Forward primer SC6:
5'- CATTTGGTTCTGGCCCACCT-3'      (SEQ ID NO: 55)

Reverse primer SC6:
5'- GTCTGCCACCAGAGCTCCTA-3'      (SEQ ID NO: 56)

Forward primer SC7:
5'- CGTCACCAAGTTCACTTC-3'        (SEQ ID NO: 57)

Reverse primer SC7:
5'- CCACCTAATTCTTCTTACAGTC-3'    SEQ ID NO: 58)

Forward primer SC8:
5'- CAAGGCTGTGACCAAGTT-3'        (SEQ ID NO: 59)

Reverse primer SC8:
5'- CTACAGCACAGTACCATACC-3'      (SEQ ID NO: 60)

Forward primer OsCc1:
5'- ACTCTACGGCCAACAAGAAC-3'      (SAEQ ID NO: 61)

Reverse primer OsCc1:
5'- CTCCTGTGGCTTCTTCAACC-3'      (SEQ ID NO: 62)

Forward primer Act1:
5'- ATGGTGTCAGCCACACTGTC-3'      (SEQ ID NO: 63)

Reverse primer Act1:
5'- TAACCACGCTCCGTCAGGAT-3'      (SEQ ID NO: 64)

Forward primer OsUbi:
5'- ATGGAGCTGCTGCTGTTCTA-3'      (SEQ ID NO: 65)

Reverse primer OsUbi:
5'- TTCTTCCATGCTGCTCTACC-3'      (SEQ ID NO: 66)
```

The PCR reaction was performed in a PTC 200 PCR machine (MJ research) using about 1 μl of cDNA, 2× Taq premix (Solgent. Co. Cat. No. EP051020-T2B6-1), about 4 pmol of each template-specific primer in a total reaction volume of about 20 μl for about 32 cycles, each consisting of about 95° C. for about 30 sec, about 55° C. for about 30 sec and about 72° C. for about 1 min.

3. Embodiments of Amplification and Isolation of Promoters

Using the isolated 2-kbp promoter sequence as a template and a primer designer 4 program (ver. 4.20, Scientific & Educational software), PCR primers for isolating about 1.8-2-kb promoters were designed. The design conditions were as follows: the GC content of PCR primers: about 40-60%, Tm: about 55-65° C., and the concentrations of salt and free Mg: about 0 and about 0.15 mM, respectively. The primers (PCR primers) were designed such that the template-specific region was about 20 bp in length and the 5' adaptor sequence was about 12 bp in length. The adaptor sequence was inserted for site-specific recombination other than existing cloning methods which are performed using restriction enzymes and DNA ligase. DNA used as a template was obtained by seeding a Japonica type Nipponbare cultivar rice, growing the plant in a greenhouse for about 3 weeks, cutting only the leap portion from the plant, and extracting genomic DNA from the leaf. The genomic DNA was obtained by freezing the cut leaf rapidly with liquid nitrogen, crushing the frozen leaf finely with a mortar and pestle, and then isolating the genomic DNA from the crushed leaf using DNAzol solution (molecular research center, Cat. No. DN128). The first reaction was carried out to isolate a specific promoter from the rice genome and performed using 32-bp template-specific primers linked with a 12-bp adaptor sequence. The primer sequences were as follows:

```
Forward template-specific primer:
5'-AAAAAGCAGGCT-tempate specific sequence-3'

Reverse template-specific primer:
5'-AGAAAGCTGGGT-template specific sequence-3'
```

Embodiments of gene-specific primer sequences were as follows:

a. APX promoter primers
   Forward primer: (SEQ ID NO: 67)
   5'-AAAAAGCAGGCTgtaaggtgacatggcatatc-3'

Reverse primer: (SEQ ID NO: 68)
   5'-AGAAAGCTGGGTccaatccgaatcaatcaatc-3' b. SCP1 promoter primers
   Forward primer: (SEQ ID NO: 69)
   5'-AAAAAGCAGGCTttgacttttctgcgaagaa-3'

Reverse primer: (SEQ ID NO: 70)
   5'-AGAAAGCTGGGTtaactcttgccggaaaagaa-3' c. PGD1 promoter primers
   Forward primer: (SEQ ID NO: 71)
   5'-AAAAAGCAGGCTtagatatgccgaacatgacc-3'

Reverse primer: (SEQ ID NO: 72)
   5'-AGAAAGCTGGGTgcagatagatgcaccaaatg-3' d. R1G1 promoter primers
   Forward primer: (SEQ ID NO: 73)
   5'-AAAAAGCAGGCTatagctgttgtactgatgtc-3'

Reverse primer: (SEQ ID NO: 74)
   5'-AGAAAGCTGGGTtctctcgcagtattaccaac-3' e. EIF-5A promoter primers
   Forward primer: (SEQ ID NO: 75)
   5'-AAAAAGCAGGCTttgttccacctcatcattaa-3'

Reverse primer: (SEQ ID NO: 76)
   5'-AGAAAGCTGGGTcaacctgccaccaacaacaa-3' f. PF1 promoter primers
   Forward primer: (SEQ ID NO: 77)
   5'-AAAAAGCAGGCTctcggtgaagatagagaagg-3'

Reverse primer: (SEQ ID NO: 78)
   5'-AGAAAGCTGGGTctcgagctgatctacgaact-3' g. PF2 promoter primers
   Forward primer: (SEQ ID NO: 79)
   5'-AAAAAGCAGGCTcaacgggacactgtcgattc-3'

Reverse primer: (SEQ ID NO: 80)
   5'-AGAAAGCTGGGTggtgccgcctcttcaaatct-3' h. PF3 promoter primers
   Forward primer: (SEQ ID NO: 81)
   5'-AAAAAGCAGGCTtcgttccaacgtaccgcaat-3'

Reverse primer: (SEQ ID NO: 82)
   5'-AGAAAGCTGGGTgggagagctgagtgagcaga-3' i. PF4 promoter primers
   Forward primer: (SEQ ID NO: 83)
   5'-AAAAAGCAGGCTtctggcatcgatatgctcct-3'

Reverse primer: (SEQ ID NO: 84)
   5'-AGAAAGCTGGGTtggagtcacgcgagatacct-3' j. PF5 promoter primers
   Forward primer: (SEQ ID NO: 85)
   5'-AAAAAGCAGGCTgctgattccgtgcacctcat-3'

Reverse primer: (SEQ ID NO: 86)
   5'-AGAAAGCTGGGTgatcctcttggacgccatcg-3' k. PF6 promoter primers
   Forward primer: (SEQ ID NO: 87)
   5'-AAAAAGCAGGCTggaccaaccgaagtccttcc-3'

Reverse primer: (SEQ ID NO: 88)
   5'-AGAAAGCTGGGTtcctgcgcttgaaggtct-3' l. PF7 promoter primers
   Forward primer: (SEQ ID NO: 89)
   5'-AAAAAGCAGGCTaactgaacagggccttacca-3'

Reverse primer: (SEQ ID NO: 90)
   5'-AGAAAGCTGGGTcggcaacgaggtcgatac-3' m. SC1 promoter primers
   Forward primer: (SEQ ID NO: 91)
   5'-AAAAAGCAGGCTgatcacttgtggcagccata-3'

Reverse primer: (SEQ ID NO: 92)
   5'-AGAAAGCTGGGTcgctagggttttgcgaattt-3' n. SC2 promoter primers
   Forward primer: (SEQ ID NO: 93)
   5'-AAAAAGCAGGCTttacgtatagccttttcctt-3'

Reverse primer: (SEQ ID NO: 94)
   5'-AGAAAGCTGGGTgacagaatatgctgtgacaa-3' o. SC3 promoter primers
   Forward primer: (SEQ ID NO: 95)
   5'-AAAAAGCAGGCTaccgatgtagatgaatacttcc-3'

Reverse primer: (SEQ ID NO: 96)
   5'-AGAAAGCTGGGTatccttccgaaacctgaac-3' p. SC4 promoter primers
   Forward primer: (SEQ ID NO: 97)
   5'-AAAAAGCAGGCTgctcgtaggacaagcaggaa-3'

Reverse primer: (SEQ ID NO: 98)
   5'-AGAAAGCTGGGTcttgcgtgctcctgatctct-3' q. SC5 promoter primers
   Forward primer: (SEQ ID NO: 99)
   5'-AAAAAGCAGGCTcctcttgccccttcctcgg-3'

Reverse primer: (SEQ ID NO: 100)
   5'-AGAAAGCTGGGTtgtgacgtggcagtctgaca-3' r. SC6 promoter primers
   Forward primer: (SEQ ID NO: 101)
   5'-AAAAAGCAGGCTgtgcactcaaggtcctatgg-3'

Reverse primer: (SEQ ID NO: 102)
   5'-AGAAAGCTGGGTtggcatacagcactccctct-3'

-continued s. SC7 promoter primers (SEQ ID NO: 103)
Forward primer:
5'-AAAAAGCAGGCTgtcgaactcaccgtgcacta-3'

(SEQ ID NO: 104)
Reverse primer:
5'-AGAAAGCTGGGTtggatgctgctctcttcttctc-3' t. SC8 promoter primers (SEQ ID NO: 105)
Forward primer:
5'-AAAAAGCAGGCTaaaaaacttgactgcccaaaa-3'

(SEQ ID NO: 106)
Reverse primer:
5'-AGAAAGCTGGGTggaaacggtggtggttct-3'

A first PCR reaction was carried out using about 50 ng of genomic DNA, 2× Taq premix (Solgent. Co. Cat. No. EP051020-T2B6-1) and about 10 pmol of each template-specific primer in a total reaction volume of about 50 µl for about 30 cycles, each consisting of about 95° C. for about 1 min, about 55° C. for about 1 min and about 68° C. for about 2 min.

A second PCR reaction was carried out to insert and amplify a specific adaptor sequence (att site) which may be used to insert a promoter into a transformation vector. The length of the sequence to be additionally inserted into the promoter was about 29 bp. To increase the efficiency of PCR, only a portion (12 bp) of the sequence was attached to the template-specific sequence by overhang and subjected to the first PCR reaction. Then, about 1/50 (1 µl) of the PCR reaction solution was taken and subjected to the second PCR reaction using primers (adaptor sequence primers) having full-length recombinant sequences. Thus, the PCR product had all the att sequences for recombination with the promoter. The adaptor primer sequences were as follows:

(SEQ ID NO: 107)
attB1 adaptor primer:
5'-GGGGACAAGTTTGTACAAAAAAGCAGGCT-3'

(SEQ ID NO: 108)
attB2 adaptor primer:
5'-GGGGACCACTTTGTACAAGAAAGCTGGGT-3'

The second PCR reaction was carried out using about 1 µl of the first PCR product, 2× Taq premix (Solgent. Co. Cat. No. EP051020-T2B6-1) and about 2 pmol of each adaptor primer in a total reaction volume of about 50 µl for about 5 cycles, each consisting of about 95° C. for about 30 sec, about 45° C. for about 30 sec and about 68° C. for about 2 min, followed by about 20 cycles, each consisting of about 95° C. for about 30 sec, about 55° C. for about 30 sec and about 68° C. for about 2 min. The PCR reactions were carried out using a Gateway system (Invitrogen, Cat. No. 12535-029) according to the method suggested by Invitrogen.

4. Embodiments of Cloning of Amplified Promoters

The promoter was inserted into a vector using a Gateway system (Invitrogen, Cat. No. 12535-029). The amplified promoter was electrophoresed on about 1% agrose gel, separated into bands on the gel and purified using the Mega-spin agarose gel extraction kit (Intron, Cat. No. 17183). A BP reaction was carried out using about 5 µl of the purified promoter, about 4 µl of a BP clonase enzyme mixture, about 4 µl of 5×BP reaction buffer, about 300 ng/2 µl of a pDONR vector, and TE buffer (about 10 mM Tris/pH about 8.0, about 1 mM EDTA) in a total reaction volume of about 20 µl at about 25° C. for about 16 hours. Then, about 6 µl of an LR clonase enzyme mixture, about 1 µl of about 0.75 M NaCl and about 450 ng/3 µl of a transformation vector were added to the reaction product and subjected to an LR reaction in a total reaction volume of about 30 µl at about 25° C. for about 8 hours. About 3 µl of proteinase was added thereto and allowed to react at about 37° C. for about 1 hour, and then about 2 µl of the reaction product was taken and transformed into DH5α competent cells. The transformed DH5α cells were plated in LB agar medium containing about 50 µg/ml of a Spectinomycin antibiotic and were grown in an incubator at about 37° C. for about 12 hours. DNA was extracted from the selected cells, and whether the promoter has been inserted into the extracted DNA was confirmed by PCR. Then, the DNA was subjected to sequencing and BLASTN analysis to confirm complete insertion of the isolated promoter.

A vector (pMJ401) is described as follows. Between the right-border sequence and the left-border sequence, a cassette to be replaced with a promoter according to embodiments subsequent to recombination is linked with the visible marker gene GFP and a protease inhibitor II at the 3' end. The cassette has the att sequences to facilitate BP and LR reactions. The selection gene (selection marker gene) was prepared such that the herbicide-resistant gene bar (phosphinotricine acetyltransferase gene) was controlled by the constitutive expression promoter OsCc1 (see U.S. Pat. No. 6,958,434). The gene was linked with a nopalin synthase (NOS) terminator. Also, a MAR sequence was attached to the terminal of the right-border sequence to minimize the change in expression in various sites of the chromosome, such that only the inherent activity of the promoter could be measured.

5. Embodiments of *Agrobacterium*-Mediated Transformation of Rice

About 70% (v/v) ethanol was added to T0 hulled rice seeds (*Oryza sativa* L. cv Nakdong) and gently mixed for about 1 minute to wash the seeds. The washed seeds were sterilized by treatment in about 20% chlorax for about 1 hour and washed several times with sterile water. For transformation, the washed rice seeds were incubated on a callus induction medium (2N6) for about one month according to the method of Jang et al (Jang, I-C. et al., Mol breeding, 5:453-461, 1999) to induce embryonic callus, and then were co-cultivated with *Agrobacterium* obtained by an *Agrobacterium* triple mating method so as to insert the promoter-inserted transformation vector into the rice genome. Then, the plant was incubated on a 2N6-CP medium for selecting transformed callus for about one month. The grown cells were selected and cultured in a redifferentiation medium (MS-CP) for about 1-2 months, and a redifferentiated plant was acclimated in a greenhouse. The acclimated T0 rice was treated with the non-selective herbicide basta, and only the plants showing herbicide resistance were selected and subjected to a progeny test.

6. Embodiments of Analysis of Promoter Activity by RT-PCR and Real Time qRT-PCR

For the analysis of promoter activity, total RNA was extracted from the seeds of transformed plants and the leaf, root and flower tissues of 5-day-old, 20-day-old, 30-day-old and 60-day-old seedlings. An RNeasy plant mini-kit (Qiagen, Cat. No. 74904) was used to extract the total RNA from each tissue. A first-strand cDNA was synthesized using about 400 ng of the extracted total RNA (Invitrogen, Cat. No. 18080-051), and PCR was performed using about 1 µl of the synthesized cDNA product as a template. The PCR reaction was performed using two kinds of primer sets. The first primer set was a primer set (primer GFP) for comparing the expression levels of GFP inserted downstream of the promoters, and the second primer set was a primer set (primer Ubi) as a cDNA loading control. The primer sequences were as follows.

```
Forward primer GFP:
5'-CAGCACGACTTCTTCAAGTCC-3'        (SEQ ID NO: 109)

Reverse primer GFP:
5'-CTTCAGCTCGATGCGGTTCAC-3'        (SEQ ID NO: 110)

Forward primer OsUbi:
5'-ATGGAGCTGCTGCTGTTCTA-3'         (SEQ ID NO: 65)

Reverse primer OsUbi:
5'-TTCTTCCATGCTGCTCTACC-3'         (SEQ ID NO: 66)
```

The RT-PCR reaction was carried out in a PTC 200 PCR machine (MJ research) using about 1 μl of cDNA, 2× Taq premix (Solgent. Co. Cat. No. EP051020-T2B6-1) and about 2 pmol of each template-specific primer in a total reaction volume of about 20 μl for about 39 cycles, each consisting of about 95° C. for about 30 sec, about 55° C. for about 30 sec and about 72° C. for about 30 sec.

The real-time qRT-PCR reaction was carried out in Mx3000P (Stratagene) using about 1 μl of cDNA, 2×SYBR green qRT-PCR premix (Invitrogen. Cat. No. 11765-100) and about 2 pmol of each template-specific primer in a total reaction volume of about 20 μl for about 40 cycles, each consisting of about 95° C. for about 15 sec and about 60° C. for about 30 sec. After completion of the reaction, the promoter activity was quantitatively analyzed using the program Mx3000P (Stratagene) according to the manufacturer's instruction.

7. Embodiments of Observation of GFP Expression and Analysis of Promoter Activity in Each Organ of Rice For the analysis of promoter activity, the expression of fluorescence of the marker gene GFP was observed in seeds and the leaf, root and flower organs of seedlings which were about 1 month old after germination. The observation of gene expression was carried out from the T2 generation in which the insertion and separation of the gene could be reliably observed. The observation of GPF expression in seeds was carried out by hulling the seeds and observing GFP expression in the embryo and endosperm of the hulled seeds using an LAS3000 system (Fuji Photo Film Co., Ltd.) and a SZX9-3122 stereomicroscope (Olympus, Tokyo, Japan). Meanwhile, in order to observe GFP expression in seedlings which were about 1 month old after germination, seeds in which GFP expression has been observed were selected and sterilized in ethanol and about 20% chlorax solution. Then, to examine the activity of the selection marker "bar" gene, the selected seeds were germinated in a PPT-containing MS-P medium (about 4 mg/l PPT) in a dark condition for about 3 days, and then incubated in a light condition for about 2 days. The germinated etiolated seedlings were grown in soil for about 25 days, and then the expression of the gene in the leaf and root of the seedlings were observed using an LAS3000 system under the following conditions: precision, standard, exposure time: about 1 sec (excitation filter: about 460 nm, and barrier filter: about 510 nm). Flowers were collected before opening from the seedlings and observed using a SZX9-3122 stereomicroscope (Olympus, Tokyo, Japan) before and after removing the glume. In this way, GFP fluorescence in each organ in rice was observed.

EXAMPLE 1

Analysis of Expression of Genes in Each Rice Tissue

To examine the tissue-specific activities of the APX, SCP1, PGD1, R1G1 and EIF-5A promoters, samples were collected from the seeds of the transformed rice and the leaf (L in FIG. 1), root (R in FIG. 1) and flower tissues of 5-day-old (or 7-day-old), 20-day-old, 30-day-old and 60-day-old seedlings, and total RNA was extracted from each sample. cDNA was synthesized using the RNA as a template and amplified by PCR. The PCR products were electrophoresed on about 2% agarose gel.

FIG. 1 shows the results obtained by comparing the expression patterns of twenty constitutive expression genes in various tissues of rice using RT-PCR. As can be seen in FIG. 1, the APX, SCP1, PGD1, R1G1, EIF-5A (indicated as "EIF5" as the figure; hereinafter the same), PF1, PF2, PF3, PF4, PF5, PF6, PF7, SC1, SC2, SC3, SC4, SC5, SC6, SC7 and SC8 genes used were expressed substantially uniformly in various tissues of rice. Also, these genes showed expression patterns similar to those of related constitutive expression genes OsCc1 and Act1, suggesting they may be constitutive expression genes.

EXAMPLE 2

Construction of Rice Transformation Vector and Structure of Promoter

Figure 2:
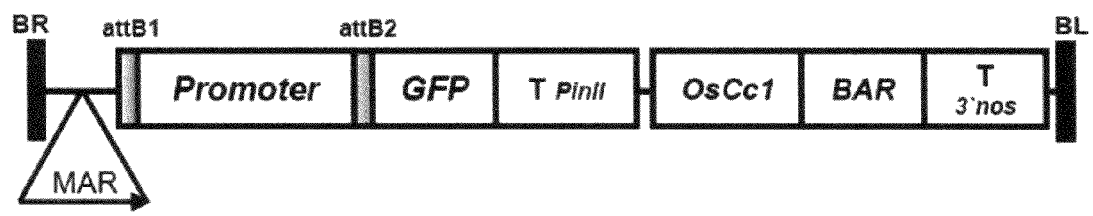
FIG. 2 is a schematic diagram of a vector according to embodiments.

A vector for analyzing promoter activity was constructed and is shown in FIG. 2. FIG. 2 shows a pMJ401 vector. The vector may be a parent vector for cloning the isolated promoter by PCR. The attR1 and attR2 sites are sites where recombination (site-specific recombination) with the attL1 and attL2 sequences of the promoter may occur after a BP reaction. After an LR reaction, a cassette was replaced with the promoter and the attR1 and attR2 sequences were also replaced with attB1 and attB2 sequences.

Figure 3:
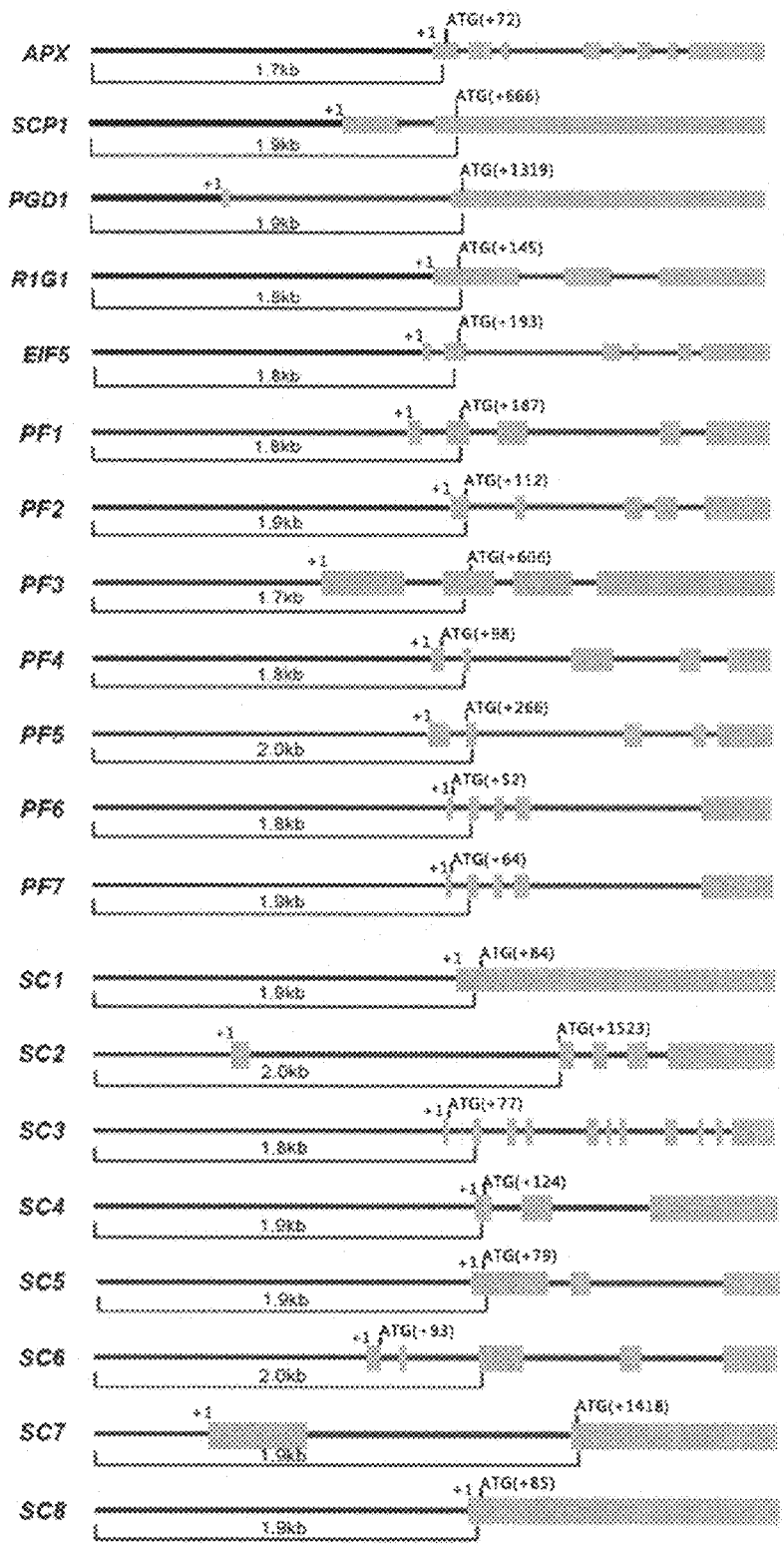
FIG. 3 shows structures of promoters according to embodiments.

A description is provided as follows: MAR: matrix attachment region (1.3 kb), X98408; cassette B: conversion cassette B (1.7 kb; Invitrogen, Cat. No. 11828-019); GFP: modified green fluorescent protein gene (0.74 kb), U84737; TPINII: protease inhibitor II terminator (1.0 kb), X04118; OsCc1: cytochrome c promoter (0.92 kb), Af399666; BAR: phosphinotricine acetyltransferase gene (0.59 kb), X17220; and TNOS: nopaline synthase terminator (0.28 kb). FIG. 3 shows the structures of embodiments of promoters disposed in a rice genome.

EXAMPLE 3

Figure 4:
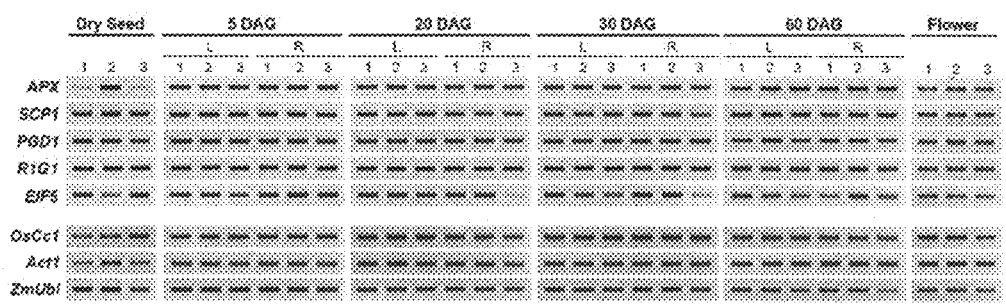
FIG. 4 shows results of Green Fluorescent Protein expression levels using RT (reverse transcription)-PCR in seeds of a transformed plant according to embodiments as well as the leaf and root tissues of 5-day-old, 20-day-old and 30-day-old the plants.

Analysis of Promoter Activity (e.g., GFP Expression Level) in Each Tissue of Transformed Rice by RT-PCR RNA was extracted from the seeds of the transformed rice and the leaf, root and flower tissues of 5-day-old, 20-day-old, 30-day-old and 60-day-old seedlings. cDNA was synthesized using the RNA as a template and amplified by PCR. The PCR products were electrophoresed on about 2% agarose gel. Each PCR product was loaded in an amount of about 5 μl. FIG. 4 shows the results obtained by semi-quantitatively analyzing the GFP expression level caused by each promoter in the rice seeds and the leaf (L), root (R) and flower tissues of 5-day-old, 20-day-old, 30-day-old and 60-day-old seedlings using RT-PCR. GFP was a PCR product amplified with GFP primers and was used to compare the expression levels of the GFP gene inserted downstream of the promoters. The PCR product was 141 bp in size. In view of the difference in gene expression according to the variation between events, the analysis of the transformants for each promoter was carried out using 3 events having different promoter insertion sites.

FIG. 4 illustrated that, for example, APX, SCP1, PGD1, R1G1 and EIF5 promoters were novel promoters, which showed gene expression levels similar to or lower than those of the related OsCc1 promoter, Act1 promoter and maize Ubi1 promoter (ZmUbi), but induced gene expression substantially uniformly in substantially all the tissues.

EXAMPLE 4

Analysis of Promoter Activity in Each Rice Tissue by Real Time qRT-PCR

Figure 5:
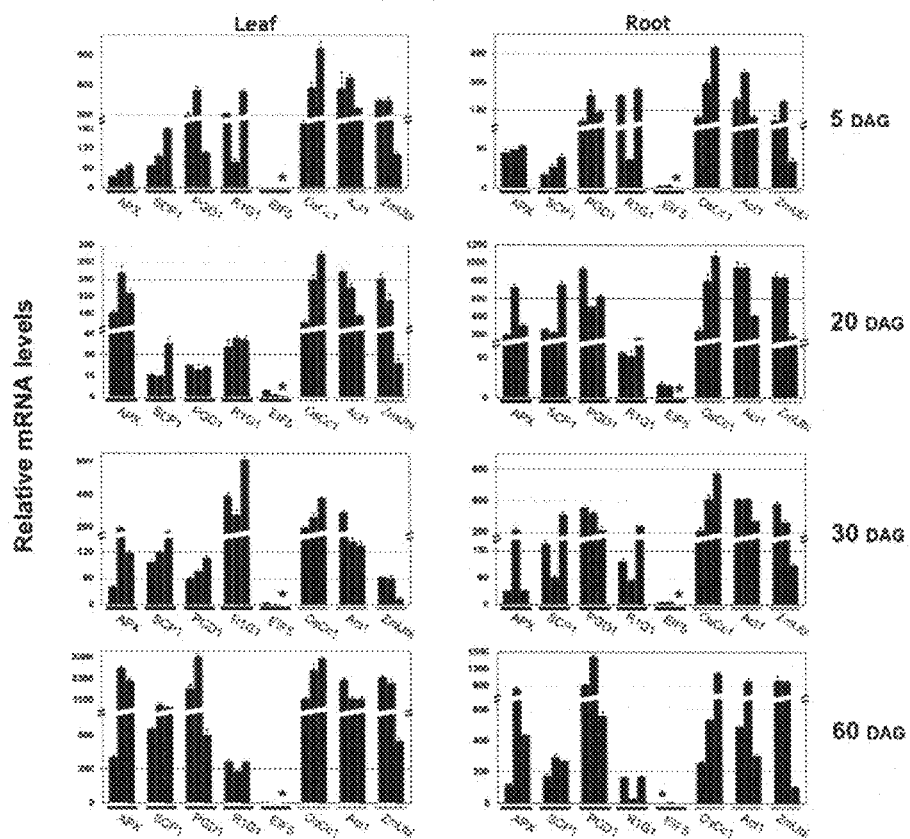
FIG. 5 and FIG. 6 show results obtained using real time-qPCR and quantitatively comparing the expression of Green Fluorescent Protein in seeds and flowers of a transformed plant according to embodiments, as well as the leaf and root tissues of 5-day-old, 20-day-old, 30-day-old and 60-day-old of the plants.
Figure 6:
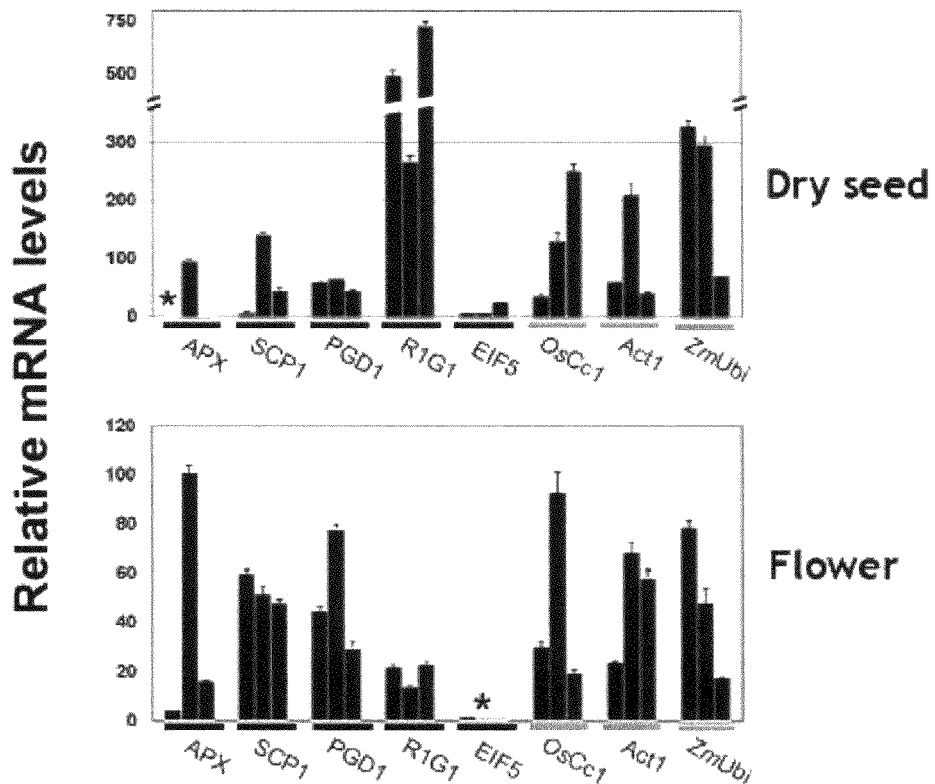

FIG. 5 and FIG. 6 show the results obtained by quantitatively analyzing the expression pattern of the GFP gene according to the activity of each promoter in each tissue of the transformed rice. Similar to in FIG. 4, RNA was extracted from the seeds of the transformed rice and the leaf, root and flower tissues of 5-day-old, 20-day-old, 30-day-old and 60-day-old seedlings. cDNA was synthesized using RNA as a template and amplified by PCR. Then, the PCR product was subjected to real time qRT-PCR analysis using gene-specific primers of GFP used as a target gene. In view of the difference in gene expression according to the variation between events, the analysis of the transformants for each promoter was carried out using 3 events having different promoter insertion sites.

FIG. 5 quantitatively shows the activities of the promoters in each of the leaf and root tissues of 5-day-old, 20-day-old, 30-day-old and 60-day-old seedlings. FIG. 6 quantitatively shows the activities of the promoters in the seed, which is a reproductive and storage organ, and in the flower, which is another reproductive organ.

EXAMPLE 5

Comparison of Promoter Activity Between Transformants Having Different Insertion Sites Because the activity of the promoter can greatly change according to its insertion location in the genome, such as the rice genome, the activity range predictable when the promoter is used to express a transgene may be determined by measuring the change in the activity of the promoter in a number of different transformants. Transformants (3-8 events per promoter) having different promoter insertion sites were grown for about 20 days in a greenhouse after germination, and then total RNA was extracted from the leaf and root tissues. cDNA was synthesized using the RNA as a template and amplified by PCR. Then, the PCR products were subjected to real time qRT-PCR analysis using gene-specific primers of GFP used as a target gene.

Figure 7:
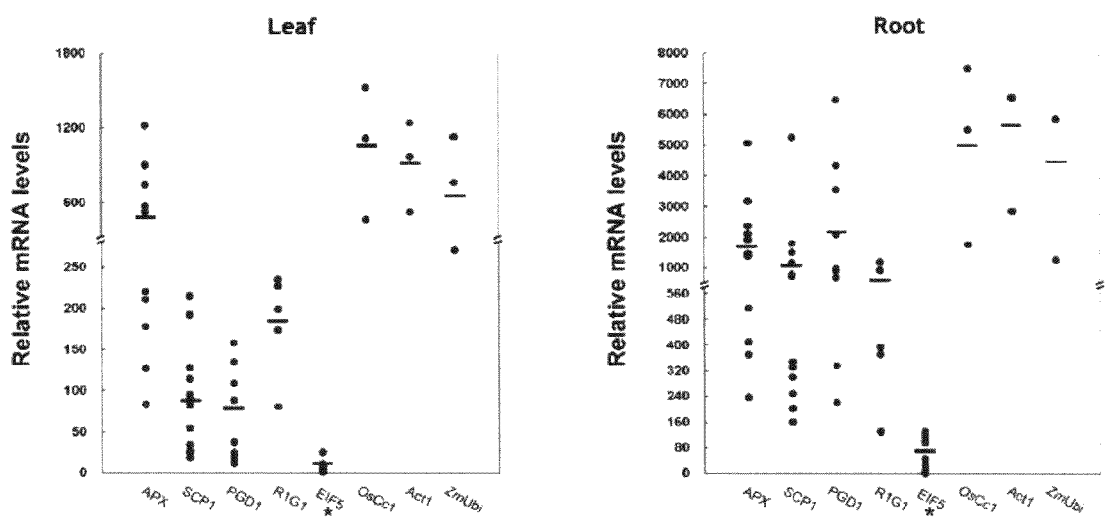
FIG. 7 is a graphic diagram showing promoter activity according to embodiments and predicted by quantitatively comparing Green Fluorescent Protein expression in several events.

FIG. 7 shows the results obtained by quantitatively analyzing the expression pattern of the GFP gene according to the activity of each promoter in the transformed rice. The obtained distribution of change in promoter activity for each transformed event may be a good index for predicting the minimum and maximum values of expression level when using the corresponding promoter for expression of a transgene.

EXAMPLE 6

Observation of GFP Fluorescence in Leaf and Root Tissues of Rice Transformed with Promoter To analyze the activities of the promoters according to embodiments, the leaf and root tissues of rice plants transformed with promoters, which were about 1 month old after germination, and GFP fluorescence in the tissues, were observed using a SZX9-3122 stereomicroscope SZX9-3122 (Olympus, Tokyo, Japan).

Figure 8:
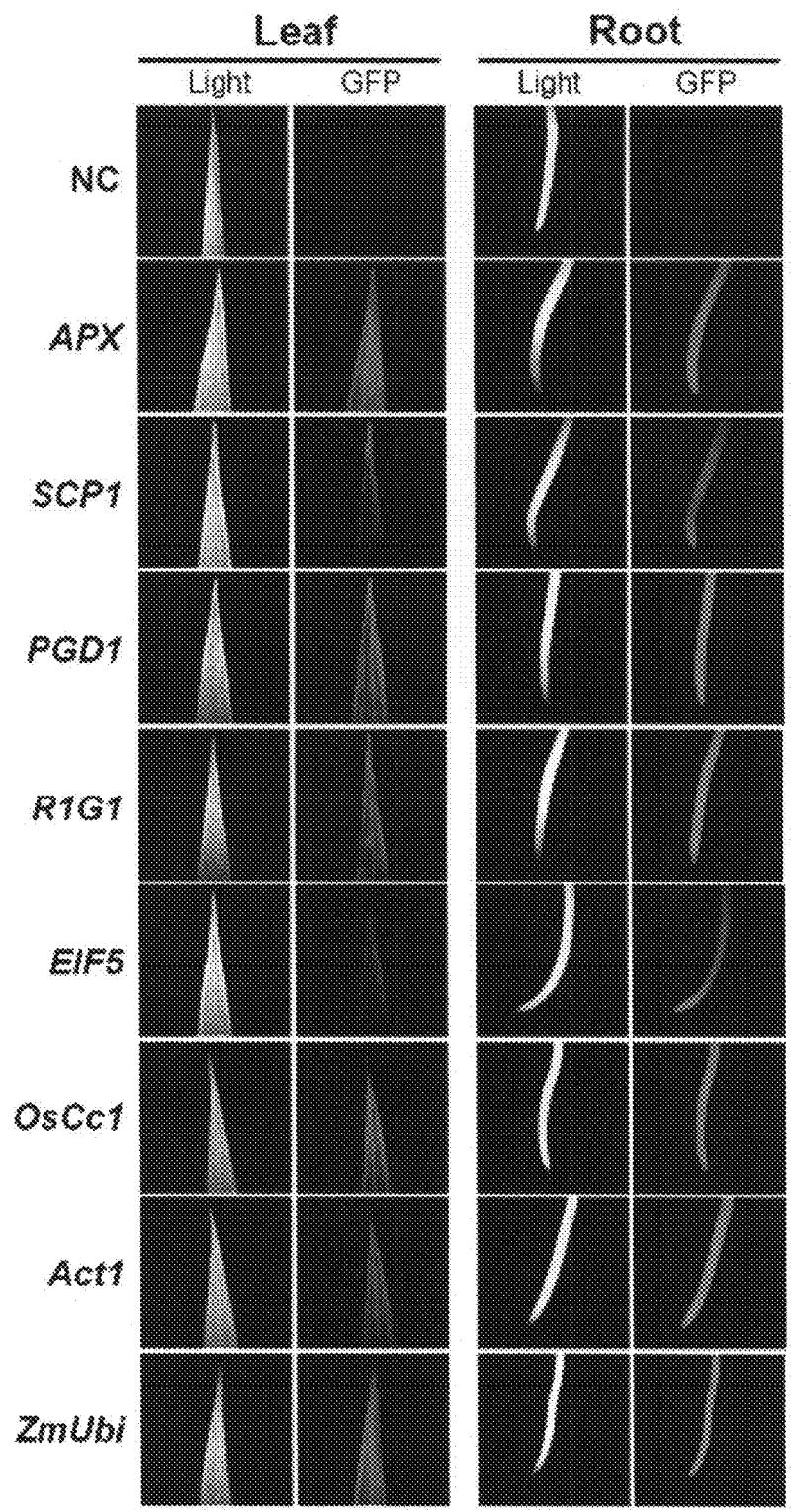
FIG. 8 shows the expression of Green Fluorescent Protein fluorescence in a leaf and root of a transformed plant according to embodiments.

FIG. 8 shows the expression of GFP fluorescence in the leaf and root tissues of rice plants transformed with promoters. The description of each gene shown in FIG. 8 is as follows: NC: negative control Oryza sativa L. cv Nakdong (non-transformed rice); ZmUbi: maize Ubi1 promoter; Act1: rice Actin1 promoter; and OsCc1: rice cytochrome c promoter.

In the leaf and root tissue of the negative control, the expression of GFP fluorescence was not observed, whereas in the leaf and root tissues of the rice plants transformed with the promoters according to embodiments, the expression of GFP fluorescence was clearly and substantially uniformly observed. This visually shows that the activities of the promoters according to embodiments were distributed substantially uniformly in the leaf and root tissues of the transformed rice plants in the same manner or better as in the case of the rice plants transformed with each of the positive controls, namely ZmUbi, Actin1 and OsCc1.

EXAMPLE 7

Observation of GFP Fluorescence in Reproductive Organ of Rice Transformed with Promoter In order to analyze the activities of promoters according to embodiments in the reproductive organ of rice, the hulled seeds of the rice plant transformed with each of the promoters were collected, and GFP fluorescence in the hulled seeds was observed using a SZX9-3122 stereomicroscope (Olympus, Tokyo, Japan). The T2 generation seeds showing homozygous GFP expression therein were sowed in a greenhouse before opening, and GFP fluorescence in the collected seeds was observed using a SZX9-3122 stereomicroscope (Olympus, Tokyo, Japan) before and after removing the glume.

Figure 9:
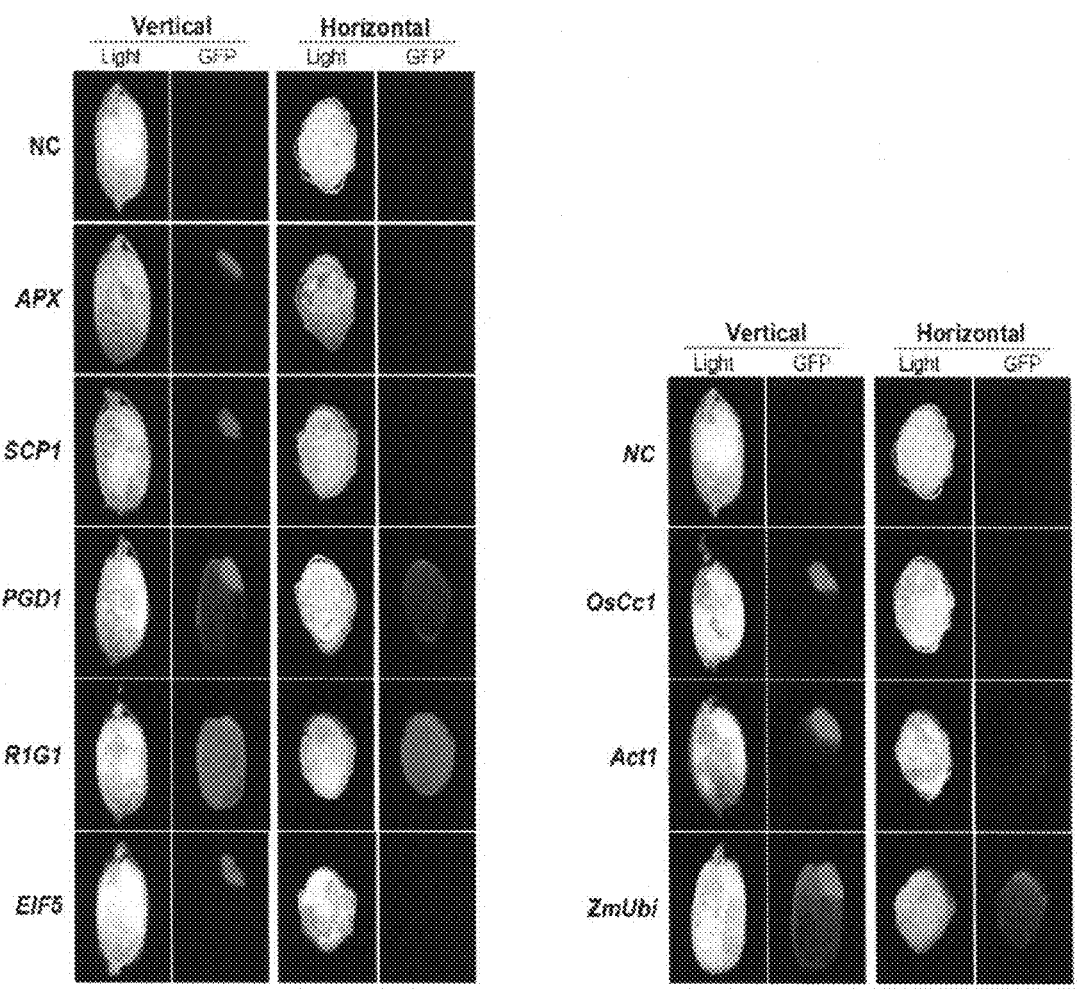
FIG. 9 shows the expression of Green Fluorescent Protein fluorescence in a seed of a transformed plant according to embodiments.
Figure 10:
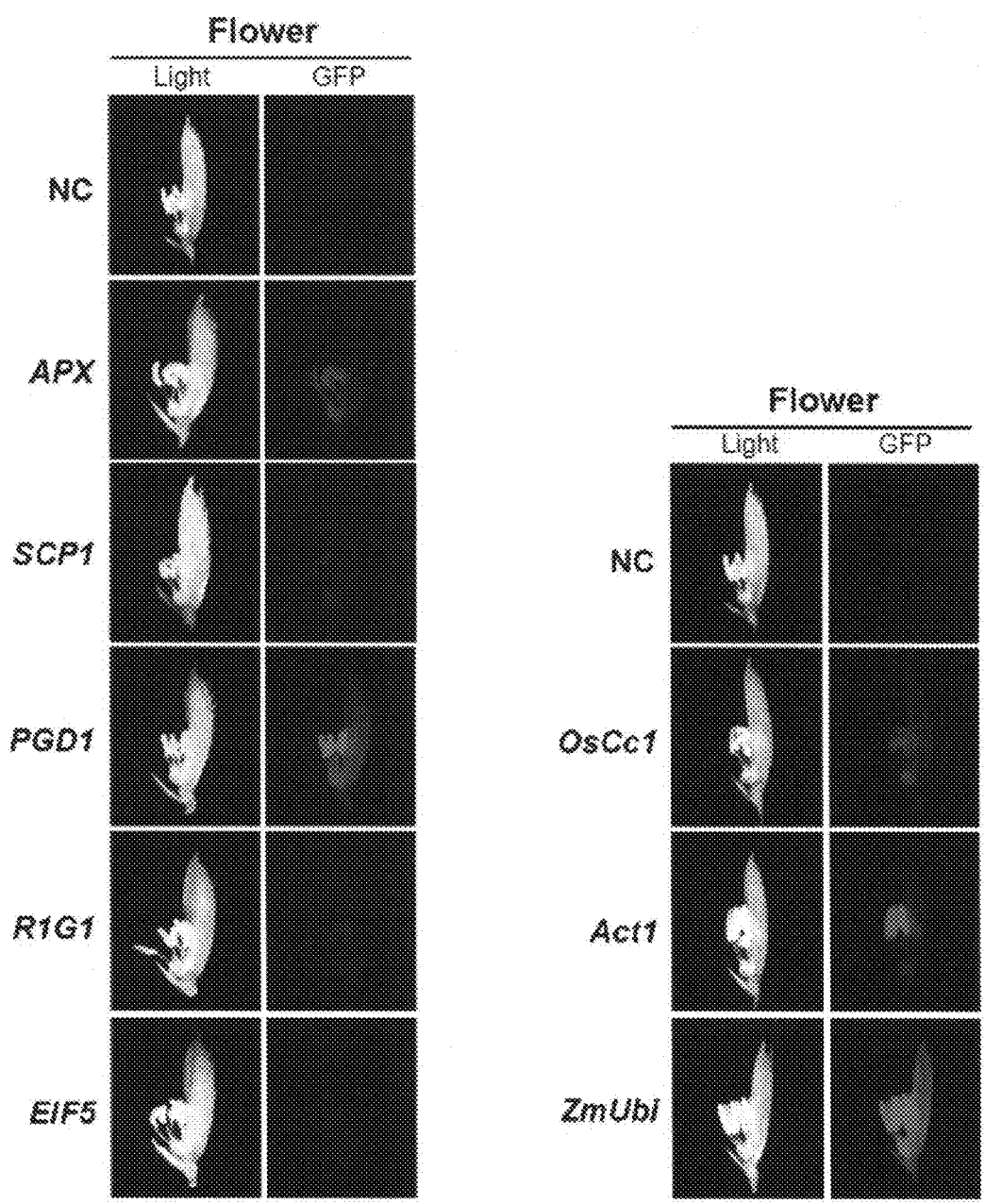
FIG. 10 shows the expression of Green Fluorescent Protein fluorescence in a flower of a transformed plant according to embodiments.

FIG. 9 and FIG. 10 show the expression of GFP fluorescence in the seed and flower of the transformed rice. The description of each gene shown in FIG. 9 and FIG. 10 is as follows. NC: negative control Oryza sativa L. cv Nakdong (non-transformed rice); ZmUbi: maize Ubi1 promoter; Act1: rice Actin1 promoter; and OsCc1: rice cytochrome c promoter.

For the rice plant transformed with the OsCc1 promoter, GFP fluorescence was observed in the rice seed, the leaf and root of the young seedling, and throughout the flower. For the rice plant transformed with the Act1 promoter, GFP fluorescence was observed not in the leaf and root of the rice plant, and also in the stamen. For the rice plant transformed with the ZmUbi promoter, GFP fluorescence was observed uniformly in all the flower organs, including lemma, palea, pistil and anther. For the APX, SCP1 and EIF5 promoters, GFP fluorescence was observed in the seed embryo in a manner similar to the case of OsCc1 and Act1. For the PGD1 and R1G1 promoters, GFP fluorescence was observed in substantially all the embryo and endosperm in a manner similar to the case of ZmUbi. For the SCP1, R1G1 and EIF5 promoters, the substantially uniform expression of GFP fluorescence was observed in the flower of the transformed rice. In particular for the APX and PGD1 promoters, outstanding GFP fluorescence was observed in the flower anther and ovary. For the illustrated five expression promoters in FIG. 9 and FIG. 10 according to embodiments, GFP fluorescence was observed substantially uniformly in substantially all the tissues of the rice plants, including seeds and flowers.

Notably, the results of expression of GFP fluorescence in each tissue of the rice plants transformed with promoters were partially different for the results of real time-qPCR. This may be a result of sensitivity differences between the analysis methods. Accordingly, the results of observation of GFP fluorescence may preferably be used as qualitative information.

It will be obvious and apparent to those skilled in the art that various modifications and variations can be made in the embodiments disclosed. Thus, it is intended that the disclosed embodiments cover the obvious and apparent modifications and variations, provided that they are within the scope of the appended claims and their equivalents.

What is claimed is:

1. A promoter consisting of:
SEQ ID NO: 3.

2. The promoter of claim 1, wherein the promoter is a constitutive expression promoter operatively linked to a gene to transform a plant.

3. The promoter of claim 2, wherein the plant is a monocot plant comprising at least one of a rice, barley, wheat, maize, millet and Indian millet.

4. The promoter of claim 1, wherein the promoter expresses a gene substantially uniformly in substantially all organs and/or tissues of a plant.

5. The promoter of claim 1, comprising a base sequence complementary to the entire length of SEQ ID NO: 3.

6. A vector comprising:
a promoter consisting of SEQ ID NO: 3.

7. The vector of claim 6, wherein:
the vector is a recombinant plant expression vector; and
wherein the promoter is a constitutive expression promoter.

8. The vector of claim 7, wherein a target gene downstream of the promoter encoding a target protein is operably linked.

9. The vector of claim 6, wherein the promoter expresses a gene substantially uniformly in substantially all organs and/or tissues of a plant.

10. The vector of claim 6, wherein SEQ ID NO: 3 is a variant having a sequence identity of at least 95%.

11. A composition comprising at least one of:
a transformed plant comprising a promoter consisting of SEQ ID NO: 3;
a transformed seed comprising a promoter consisting of SEQ ID NO: 3; and
a transformed cell comprising a promoter consisting of SEQ ID NO: 3.

12. A method comprising:
forming a target protein by transforming a plant using a vector comprising a promoter consisting of SEQ ID NO: 3.

13. The method of claim 12, wherein the target protein comprises at least one of interleukin, interferon, platelet-derived growth factor, hemoglobin, elastin, collagen, insulin, fibroblast growth factor, human growth factor, human serum albumin and erythropoietin.

14. A method comprising at least one of:
transforming a plant cell with a vector comprising a promoter consisting of SEQ ID NO: 3; and
redifferentiating a transformed plant from the transformed plant cell.

* * * * *

SEQUENCE LISTING

```
<160> NUMBER OF SEQ ID NOS: 110

<210> SEQ ID NO 1
<211> LENGTH: 1673
<212> TYPE: DNA
<213> ORGANISM: Oryza sativa
<220> FEATURE:
<221> NAME/KEY: promoter
<222> LOCATION: (1)..(1673)
<223> OTHER INFORMATION: Ascorbate peroxidase promoter

<400> SEQUENCE: 1
gtaaggtgac atggcatatc tatgtggtga ttttggtggg accaaggact atatcagccc      60
acatgacaaa tttaaaggac ttgtttggac aatatgaaag attaaggact aaaatgacct     120
aggagcgaaa ctttagggac catattggct attctccctt tttgacacga atgaaaaatc     180
caatttcata acttgtctgg aaaccgcgag acgaatcttt tgagcctaat taatccgtca     240
ttagcacatg cgaattactg tagcacttat ggttaattat ggactaatta agctcaaaag     300
attcgtcttg cgatttcctt tttaactgtg taattagttt ttcttttact ctatatttaa     360
tgctccatgc atatgtctaa agatttgatt taatgttttt cgaaaaaact tttggaggac     420
taaccgggcc taacgtgact tgaagagctg tgacagcgca aatcgtgaaa cgcggatgga     480
cctagcatta tggtgatgta ggaagtgcct tgctggcagt ggcaggtacc gtgcaagtgt     540
aataccatag atccgttggc ttatctgatt acatgatgat gattactccc tccgtttcac     600
aaatataagt cattttagca tttttcacat ttatattgat gttatgtcta gattcattaa     660
catcaatatg aatgtgggaa atgctagaat gacttacatt gtgaaacgga tcattaacat     720
caatatgaat gtggaaaatg ctagaatgac ttacactgtg aaacggaggg agtatacgat     780
tatgtaatga aaaaggagt acaatactag tcgccgtctc cccgcaaaaa aagtactagt     840
tgtcgtcaag taggggagta ataataataa taataataag ggataatata caggctgtgt     900
ttagatcgtg tgccaaattt ttttaaagta tacggacaaa tatttaaata ttaaacatag     960
actaataaca aaacaaatta cagattccat ctgtaaactg cgagacgaat ctattaaacc    1020
taattaattc gttattagca aatgtttact gtagcaccac attatcaaat catggcgtaa    1080
ttagctcaaa agattcgtct cgcgatttac atgcaaacca tgcaattgat ttttttttca    1140
tctacgttta gttctatgca tgtgtccaaa tattcgatgt gatgaaaaaa ttggtaattc    1200
gaggaaaaaa tttaaatcta aacacggcca cagtataaaa aaaaatagta gcgttgttgt    1260
ttatgaaaga ggatggtaaa gtaagacaag ataacgcaag ggcctaaaaa agtggagacg    1320
aagaagaaga cggaatatat tgcattggaa aagtgagcgc ttggacgaga gaaaaactcg    1380
gattcaagcg tccatatcag tggacaccac caatgggagg tggccacgtg ggcaggtccc    1440
gggtggaatc tggcgcgttc acacgggagg ttccgaaatt acggcaacgc cactggagtg    1500
cgaggcgcag gatgtgagat ccacgcgggg ggctccgcta ctagaaactt cttctggtcg    1560
tgggtggtac gcaccctcgc gcctcgcctt tatattacta gtaagaagat ctcatccctc    1620
cttggtgagg tgaggtgagt tgagttgggg attgattgat tgattcggat tgg           1673
```

<210> SEQ ID NO 2
<211> LENGTH: 1853
<212> TYPE: DNA
<213> ORGANISM: Oryza sativa
<220> FEATURE:
<221> NAME/KEY: promoter
<222> LOCATION: (1)..(1853)
<223> OTHER INFORMATION: SCP1 AP2 domain containing putative gene promoter

<400> SEQUENCE: 2

```
ttgactttt  ctgcgaagaa  tcctgtttac  ggcgcataat  aagatcgaag  aatcacgcct    60
aactgcatgc  agatacagtg  ccgagaacag  aatcagatct  gcggattaac  ggaagacttg   120
ttttagcttc  cgtcttttta  tctggccata  tgaaacagtc  tctcctaaaa  atagaatcac   180
tgtatagtaa  acaaatcttg  ggattgtcag  caagtgccaa  gtccacgtag  aggaaaatct   240
tccaaaatat  atcgtgggtc  atcagatgag  agattctcgc  acaaaacatg  cttacgtgtc   300
aaacgaggca  cgctacgaaa  aagaggaag  ctgaccaatc  gacggcccct  ccgtggccac   360
atgtttttgc  ccgcttttcc  aaaaaaaatt  ccgttccgtt  ttacggtgcc  cgtttacctt   420
ggccctcaag  ttagctggaa  acacaaaatc  cttccaattc  tgtcgtgggg  cctctcacga   480
taatttcagc  attaagtact  ttatttattc  taaaaatatc  tatcgccatt  tccatgtgtc   540
agaaattagt  tctgagttaa  ggacgtcttg  attgggagat  tagccttggc  cgcgtggaat   600
ctcaaccata  gaatcccaat  cccttcttt  tccgttgccc  tatcactaga  tctggtcact   660
atgcagaagt  gtaaggggcc  cacatgtcnt  gnagacgatg  atgtacaggc  caggcgtgta   720
ggtgaancnt  ttatcatttg  ctagccgcct  catctcgccc  attcgcttcc  ccgtcataaa   780
gcccccccaa  aaccctcccc  acctctgcca  tttggtgctt  atcccatga  gtggtgggga   840
cacatcgccc  gggccccaca  tgtcagctaa  aaccccgca  tgcttccgga  cggtagcacc   900
ggtaccgaga  tttttactcc  gcgaggtgac  cgctctgtca  ctgcgcgtgg  gcccggacgt   960
agtagtggcc  cacccgtcac  tgtgttcgta  gcaggcgact  gtgcagaaat  ctggtgcgtg  1020
aagccgcaga  atatcagccg  gaggcagaga  ggccactccc  gcgtgacatg  agggaccata  1080
tggtggggtg  ggcccacgcg  tcagtgtgat  ggggtggggg  ataggcgcgt  gagggagagg  1140
aatgggtgga  ggagtgggag  gggattaaat  atcggcggag  gagacgagcc  caacccctt  1200
tgctcctctc  gccgttttgg  tcggggtttt  agcgagcgcg  tgggaggccg  gaggcgacga  1260
cgacgaccgc  gccgccgtcg  gagaagaagg  ccgcggaagc  accagtacca  gcacccgtat  1320
atgtcttcta  gccccttctc  cgatctggtg  gtagtcgtgc  tcctcgtctg  cgccgtcgtc  1380
gccgcagccg  tcctcctccc  cctcgtctgc  gcccgccgat  ctatgcacca  gaggctccac  1440
ggctggaaca  agcccacgtc  gatgctcagg  tgcgtccggg  tgcccctccc  ccaccgtgaa  1500
atttttcatc  tttggcgagg  tttacgccga  tctggagtgg  atttgaccgg  gtttcgcggc  1560
cggttcgtcc  agatctggag  ggttcttggt  gggttttgt  ggggttttg  attgatgggt  1620
ttgtttctcg  tctgtgattt  tgcagggacg  ggttcggggt  caagtattcc  gggttcctcc  1680
acataaggcc  gtgtggtttc  tgtcgaggag  attgacggat  tcgatcgatt  cgtgttcgtc  1740
tccgtcaaat  ttttgcacaa  gagaaaaaaa  aagtttcccc  cttttagagt  ttttcccctt  1800
cagttttgtc  agttttgtg  aggaattta  gagttcttt  ccggcaagag  tta          1853
```

<210> SEQ ID NO 3
<211> LENGTH: 1889
<212> TYPE: DNA
<213> ORGANISM: Oryza sativa

```
<220> FEATURE:
<221> NAME/KEY: promoter
<222> LOCATION: (1)..(1889)
<223> OTHER INFORMATION: PGD1 Cytosolic phosphogluconate dehydrogenase
      promoter

<400> SEQUENCE: 3
tagatatgcc gaacatgacc aatatagaaa aggtcatatt tgtgaataga gagaagtaat      60
aatatgaata gcaaatacgg agtacgtata tagcatcata taacacatgg aagtctcttt    120
cagttagtta atctatcaca tgcgggattt gcggttaaaa gctctgttcc ccaaaacgat    180
aaactaatct aaaatcctcg caaaaaaatt taaaaaatct gtaatcttaa attcgaggaa    240
actcatgtga agaatgaggt ggtggtgacg tcaccaacaa acagatgcga aatggagaag    300
atgccctggc ctgcaactgg gccgagccgc cgttggtccg gtccacgttc tgattgccag    360
tttgccacca actccaactc catatggcac gtggggccca ccacgcccgt ggagacccag    420
gcccacaagt caggcagcaa ttttgacccg cctaccgccg ctgcggcggc tatctctgcg    480
aggcggtccg gtcccacccg tcagagagac gtcctgatcg cggcaggtgt gaaaggcaag    540
ggggatattt ggtgggctat ttaagcaggc ggtgcggtag gtggtcgact cgctgcacgc    600 cttttccgcga tttcgtcagt tacccagatc tcatcttacg caggtgagct ccgatctccc    660
ctctcccgcg ctgcgatttt gatttgatcc gtcgcgccgc atcgcgtcgt cgcttggtag    720
gatcatccat ccgtcccccg cgcagcgcga gctgtctagt ttctgctcga tttttagtt    780 cctgtttatg ggggagggag ggagagaggg agggattggg tggaggcgaa ccaggaatcg    840
tcctggcggt gtgatgtctg gatgaattgg attggcagcg tcttttagtg gctgagagat    900
tgtttccttg ttactgttcc gtggggttta caactttaga atttgtttct tcgacagcat    960
gcagcaactt ggtagaattt agctgcatgt tctaggtggt ttgttgctgc tgatcctgct   1020
cgtttggatc aacgatttt gggggctga gattaattgg ttggtacagt cttggttagt    1080
tacatccatg ggaacatgca gttggttatt ggtttgcaca tggagtacta ctgctaatgg   1140
ggtagatata gacagtgtgt gcgccaaagc ttgctaccac tagtttcttt aagtatagtg   1200
cctcccaatt accaatatta cctatttttca gtgtaaagtg ttaaatagaa agattgcttc   1260
tgattgctat ctcctttact gaattggtag ttaggtgcac atcttccatt gtaacgtatg   1320
tgttaccatg gctcatgtac tagttatgct agatatgttg tgctgctaaa catatatact   1380
agaaagaatg ctaccactcg ttccttctgt tgttaattgt ggaatgtttt gcaatctcta   1440
gtttgtagct cacaactgac catatgattc cccatccaag tgtcgacctc atgtgtgatt   1500
tcataaataa aaaagagcat atttttcagga tcctgttatg atcctcattt catacattta   1560 tataccttt ccataataca tgaatgatgc ctcactcaat gctataaatg ttcacattat    1620
atattacctc ctcctacaag tatgaaatat gaattgccat aggccataca aaagagccca   1680
ctccctatat tggactcgat aaatatttt agtacatagc tcttaacttg catgtcatag    1740
tctgatgtac tgtccttttt gaattggaaa ctctgttact ttataaaaag gattgacatt   1800
tgtattccat tgttaaaaga aaagcaacat ctgcacaaac tagtttgttc tgcgcatgat   1860
gtattgatac atttggtgca tctatctgc                                    1889

<210> SEQ ID NO 4
<211> LENGTH: 1800
<212> TYPE: DNA
<213> ORGANISM: Oryza sativa
<220> FEATURE:
<221> NAME/KEY: promoter
<222> LOCATION: (1)..(1800)
```

<223> OTHER INFORMATION: R1G1 putative R1G1 domain containing protein
      promoter

<400> SEQUENCE: 4

| | | | | | |
|---|---|---|---|---|---|
| atagctgttg | tactgatgtc | gtgcctaatg | aggaaattgg | agtaactgtc | taactgattc | 60 |
| aacagaggaa | attaaatcca | ggtgagggat | gatcagtgaa | tccaaatatt | gtactaatga | 120 |
| tcatgagtat | tttatgtggg | cattcttctt | gacttgaagt | tgtaaccgga | cataactgct | 180 |
| gctaggaatg | tatgacttga | agctttaagc | actactacat | ctgatgatcc | ttacatgttg | 240 |
| agcaagaggc | tggaagaaaa | aaaggatgag | agccttttaa | cccatgtaac | tccaatgctg | 300 |
| tctgcaaacc | tttcagctgg | ttgtgagttg | tggctgcaga | tctgtggaag | ccactgagag | 360 |
| agcactaggt | aaggtttcta | tgttatatct | gtaattctgt | atatgtttaa | tgtgttgtgc | 420 |
| tcatttaaaa | aagaactgc | atagattcac | aaactgcctg | gagctttcct | cttcactttg | 480 |
| ctaatagtat | tgaccacgtt | ttgggcttgt | tgtgtgtttg | gaaggagtgg | gtctataggc | 540 |
| cgtcagtgtt | taggcctact | aattaagcca | gttcagttgg | gccttggctg | cttccatgga | 600 |
| ttaattatga | gactaatcgc | agatactcgt | acaccaatgc | gagaatttgt | caaatcaatt | 660 |
| ggatcagtat | atatcttgcc | tgtatgattc | acatccatac | gtttctatcg | agttggttgg | 720 |
| aagatttgtg | ccgtcgatga | cagtgcagaa | gagaagcttc | cttgcaacta | gtgtcgtggc | 780 |
| agaagcagag | gtagacacat | gaaatcgtgt | tctaatccgt | cgcagctagc | tagcatggca | 840 |
| gcgacgtgtt | tgacgatgac | accaccttgc | atatccagat | gcctctgttt | gacctggatg | 900 |
| gaacaaacaa | taacgtacgt | ttttcgagca | tctaaatggt | ataaattttt | agagaaattt | 960 |
| ttatgtgtaa | tttcttttctt | ataatatagt | tttaaaatct | gtttcacaac | taatcaattc | 1020 |
| agtcgtttgt | atcctcgaat | cattttcatg | ttcaacattc | catccattta | ggcatttatg | 1080 |
| cacagaacag | tagaatacat | agtttgtcca | tgctttaaac | gaaaagtaaa | aagaaagag | 1140 |
| aaagacacat | attcctctta | aaacaatatt | cgtttgagat | ggtggaggga | acaaaggcca | 1200 |
| ttgatttgct | gcagggtccc | tccctaacaa | gctgtgatga | ttctgtatac | gacgatcgtg | 1260 |
| caattaagct | agtgctttga | aagagacaga | cagacagaca | acttttttcc | tcctaatacg | 1320 |
| atcggaagaa | aactgtcgag | cttttatgta | gcgtataaac | cttgactgtt | gcgaggaaaa | 1380 |
| aaaagctgta | ggaaacaaag | aaatcgagga | aatgaatttg | tcctggtttc | gtatatatgt | 1440 |
| acatgtacta | tatgccaaaa | acgcccgtgc | ttaacagcta | agaaatcggc | caaaattcag | 1500 |
| gcaaacaaga | gacaaagtta | gcaggcaacg | cgtcactacc | gcgtgatcat | ttcgacgcga | 1560 |
| aggcaatttg | gccggtgatc | cagcgcgtct | cgtgcagtga | atgaagtagc | ttaatttgct | 1620 |
| agtccccaca | agtacgtggc | actctgccat | gtcttctctt | agtataaata | tatggaagcc | 1680 |
| aaagccaaag | ccagtcagtt | catcagttgc | agttcagagt | tgcccactgc | tactttactt | 1740 |
| tgcagctatt | ttgcttctgc | ttcttcttgt | tcttgttgct | gttggtaata | ctgcgagaga | 1800 |

<210> SEQ ID NO 5
<211> LENGTH: 1837
<212> TYPE: DNA
<213> ORGANISM: Oryza sativa
<220> FEATURE:
<221> NAME/KEY: promoter
<222> LOCATION: (1)..(1837)
<223> OTHER INFORMATION: EIF5 translation initiation factor EIF-5A
      promoter

<400> SEQUENCE: 5

| | | | | | |
|---|---|---|---|---|---|
| ttgttccacc | tcatcattaa | gaaagcattc | aatctaccta | ctgatcatct | cgcttgcacg | 60 |

-continued

```
ttttcagggt agaggagcac cagatatttt tcgaaatgaa gcagcacttc taaggaggtg      120
tgcctcacct tttagcagga ggtccctacc ttcatgttgt acaactaatc gagctaaact      180
tattcgtagg tattcttttc cacccatca ttttgttagc tgcgcaggat gtagctgaac       240
gttgttgtat tgttgtatgg ggaagcatta tactcataca aattagcagg tttacctatc      300
tcagcttgtg taggcatgtg attgttctca agcaagggca gggtagattt gtagcgactg     360
tgtgtaaact agtacatcat gtactgtatg ttcaaactgc tattaggaaa tgtaacacat      420
gttattggac atttggactt ggatctggtt atgcaaaatg gttgaagcaa atttgagttt     480
ttcttttctg ctagtaggga aacgagtagg aatatttact cgagaggaat cttttgcttc     540
tcaagcacat tctttctttt ggagttgatc cagacattga attgtgtctc ttttggtgtt     600
gctccagaca tattgaagtg tgtgtatctg tttgacctga tgcgtttgcg tctggaatct     660
ttgctgcact aggatgctgt gacttccagc tagtgctatg ttgctagtat ctggctttcc      720
ccttttctgg gttttcacc atttgatctt ttagaacatt tatttaacaa atagataaaa       780
aaaagactta ttctgattct ttttttggca ccaccgttat tggtctcgtg gttcaacatg      840
accgtgccaa tgacattggc gctgttctac attctccggt ggactaatgt gaagtgatgc      900
caatatcatt ggcgttgtta cgttggacca caacgtcaat aatgttaatg ttgtgaaaat      960
gatttattcc taaatatgtt ttttaattc tattttaaa atcaattttt taaaaggat      1020 ataatgtgaa aaatctggct ccccattctt agggatgtaa attttcagac ggtaaccta     1080 ctgcttaaaa gtattatgga aaggctcacc gggggtatgt atggatcatg tcaaatgact     1140
cagtagagca caaaagtgct ttctgggttt atcttaacct ttgtaccgtc catttatcgg     1200
taggagaaca cgtgccattt tttgctggct tacagatata tcgtgacagg tgacaaacac     1260
gcaaaggtac atttcagccg accaaaaaaa atgttgtaca gtgaactgca atntgcaatt     1320
ttcatcgtgc actactcctg ctagtgcacc acgacgacac gcaatcccag gcgaagcggc     1380
ttctgcgcgc tgcgaaaagt cagcagcaaa accgccgcct gccgttgggt gggccccacg     1440
tctatgaaaa ggacgagccg cttttgtctc acgtgcggcc ggatccggct ggacccttc     1500 gatccgacgg ctacgctagg tacgcgcggg cgccaccccgg ccgaccaaag taactatcac     1560
gacgggccga ccgaatgggg ccggcggaaa agcccatccc acgggcccgct ctccgcggat    1620 gcggcgcctc atacataaat gtctcgctga gctccgcccg tccggaaccc tagtcgccgg     1680
atcgcgtctc tcccatcctc tcgcgcatcc tcctccgact acctcggtga gccgccgccg     1740
cctcttccac tctcgtcttc ttgatctgat ctaggggggtc gcggcgttcc tgacctgtgc     1800
gcgcctggtg gtggttgttg ttgttggtgg caggttg                              1837
```

<210> SEQ ID NO 6
<211> LENGTH: 1813
<212> TYPE: DNA
<213> ORGANISM: Oryza sativa
<220> FEATURE:
<221> NAME/KEY: promoter
<222> LOCATION: (1)..(1813)
<223> OTHER INFORMATION: PF1 promoter

<400> SEQUENCE: 6

```
ctcggtgaag atagagaagg tttagaaaat acatggttga acccaacaat tgtaccaagt       60
tcctccaccc attcaacgaa ttggccttca tcttttggct actaaaatca gcccatgacc      120
cccccccccc ccgcctcgat gaatattttt ttgccacttg ccttctctta tttgatgact     180
ctactgcgga caagattctt ctaacatatt attgcccctg atatgatcac taatatgtgg     240
```

| | |
|---|---|
| aggtcatcgt caatcgtcca catgactctt taagtaaatt aagtaaaagg atctcaatct | 300 |
| ctcaggtgtt gtctcttccc tttgattgct tgagtacctt ggtggctatt tgtgtctttt | 360 |
| gacttgaaga tgggtgcgt tcgtctcgtt tgccgtgagt ctacaaaact atgagcttcc | 420 |
| tctaattcaa acccgcgtgt ttctaatcct cttcgtctca tagcctacaa cgcaagagtc | 480 |
| ttgatggttt atttctttta ccacatcatg tgacgcttac gatgttagtt tattatagat | 540 |
| ataatgcaca atttgttact ctattagtta acatgcaaag ttttgtagca gtagcctcct | 600 |
| atcatatctt gaaagttttt ttttacattc atttattttg cacgagaaat cctaccgtat | 660 |
| ccttatgttt ttggtacact cttgtgtttc caaggagcgt tgactattcg gcttgaataa | 720 |
| aggtgtgttt ggttgggtgg atggagcatg gataggagat ggccacccga gttttttgtgg | 780 |
| tgtttggttg gagggcaagg tggatggggc agcctagaat agggaatatt ccctcaatat | 840 |
| gctggatgag tgcatccggc cgatttggct ggatgaatcc atccagtttt ggactgggtg | 900 |
| atatgtccta ttccgattgg ctgtggttgg tttgatttcc tgttaagcaa gctccaaatg | 960 |
| atttttttct cctaaactgt ttgtctaatt tatgatttga ttacaccatt atattcgtta | 1020 |
| taattaaatc tttaaaacaa gatttcggat gattatattt tgataaaaaa aatatatatg | 1080 |
| ataaatgagt cccactaact tttggctttt cgtatctatg ctatatccct ccaaccaaac | 1140 |
| aagaaattgg atcgccatat ccatacaaac caaacagaaa attggatcgc cgtatccaat | 1200 |
| aaaatatgga tgaccatatc ctatccatgc atgaccgtga atcaaacaca ttataatagg | 1260 |
| cctccactca cgaatctgat catgggcttg tgcctgccag cctatgcatc attacttaat | 1320 |
| gggcctggac ccttaaattg tccaagttca tcacgcaaac aagatgtggc ccgtatcgga | 1380 |
| gattccctca cgaaaaggg cccatctccc ccgggctgct cggacgatgg cccacatact | 1440 |
| cacggcccac cgtatcctat cgtgcccat ccaaacacgc gcaaacaccg cacgtgcctg | 1500 |
| acccaaactc cgcaaacggg ccggatccga accagacgag gcccacgatc cggcccaaga | 1560 |
| ggagaaaccc tagcgaggaa gggagtgcct cctacccgct ataaattccc agccacgccg | 1620 |
| cctcctccca aaccctagaa gccccctgc ctcctgcgcc tccgccgccg ccgccttctt | 1680 |
| cgtctgctgg tacgccgccc ttcgccgccg ccgcctccgc atccaatctg cgttgttctt | 1740 |
| ccgccgattt cgattgcctc acccttcgtt ttgtttcttg attgatctcg cagagttcgt | 1800 |
| agatcagctc gag | 1813 |

<210> SEQ ID NO 7
<211> LENGTH: 1894
<212> TYPE: DNA
<213> ORGANISM: Oryza sativa
<220> FEATURE:
<221> NAME/KEY: promoter
<222> LOCATION: (1)..(1894)
<223> OTHER INFORMATION: PF2 promoter

<400> SEQUENCE: 7

| | |
|---|---|
| caacgggaca ctgtcgattc ccctcgcccg ctccctcccc attactccac ggcaacgggg | 60 |
| aggggatcca ccggcagcgc cgcttcccct cggccactcc ctcacccatc ctccaccagc | 120 |
| tccaccggcg gcgctctccc tctcggcaca gagtcggcgg ccctccgccc cttctcgcct | 180 |
| tcttcccgcg ccagatcagg cgggtggagg agtcggtggc ggtggcttcc tccgcccct | 240 |
| ctcgccttcc ttccgccaca gatcgggcgg cggtggcggc cgcggctgga ttcggtggcg | 300 |
| gagaacggat tcgcggcag tggcggcggc tccttccacc ctcgcctccc tccctcggca | 360 |
| gaaacgacag cggtggcgag cggcggcggc gtagctcggc aagccacgac tggcggccac | 420 |

```
tccatgcccc ctcctcgtca gatctggcca tgggagacgg tggcggctgc ggcaaactcc    480
gctcgatttt tggtcaattt gttttttta atctccgttt gctgttcttc tattcttgta    540
tttgggatca aacttgatta aaactttgtg tgttatttgc tgcggactct ggatgatttg    600
ttgtgtgttc ggacttatga tgttgtggac aaaaataggt gaagacggac gaaacacctc    660
acggaatcct tgtgttattt gatgcggacc ctggatgatt ttttatgaa cattatggac    720 tgttttaat cggacagatt cggttttttt tcgccctttc tttttaccat gtcgcatata    780
atcggattcc attttttgc ccgattcttt tgtcgcctat tttttcacgg acggatgacg    840
gaaacactcg taattttgta agtggtagag atttttttcct tttttacata agacggaaac    900 tctttttcg cactccttt taatcgacca gaatttttt tgcactttt ttggatcttg    960 gtttttttg gcacagacga cggattttt taatcggaca gaataattt tcgcgttat    1020 tttttccttt tttacggaag acagaaaccc ttttttgcc ttttttaat cggacagaaa    1080 tttttcgcac tttctttgt cgcttgtttt ttcgtacaaa aatcttttt ttggcactct    1140 tttttgaagt cggaaaccgt ttttcgcacc tttttttttc tgggaatcgg acagaaaata    1200
tttttcgcac tttttttgg aaattttct taacttttta agtagcagag atagagatat    1260
atgcacgtgt tctcctggtg atgctaaccg aataggaccc ggattttcta gatcggacag    1320
ttttggtttt tcttttcttt ttccgcactt cttttcgcc cggttttta tcggacaaac    1380 ctgattttt tcgttcggtt ttttgatga acgatggaag cacctcttt ttaagtagta    1440 gaggtagaga ttcatgatcc tttaacactg aatgatggcg aaagcggaca agtccaaacg    1500
attccgtgcc gccccgctg acctcccttc ggccgccaca aacgcatctg agccgtccgc    1560
ctccgaatat ccgtcccaa tatcccgatc ggacggcagg caatcaacca cgtactcctc    1620
ccggcttctc ccccactcaa aagcccaaac cggcacaaat cggagatctg ggccgtccat    1680
cggtaatatt cccacggcat cagccagatc ggacggccag aatcgcggcc cagatatttc    1740
ggcccgctta taaataccgg ctggtcgcct ccacctcaaa ccctctctct ccgtccgtcc    1800
gcgccgctac tcccccctcg ccgagagagc tctagggttt ccgctgccga attttttttt    1860
taattcgggg ggagagattt gaagaggcgg cacc                              1894
```

<210> SEQ ID NO 8
<211> LENGTH: 1747
<212> TYPE: DNA
<213> ORGANISM: Oryza sativa
<220> FEATURE:
<221> NAME/KEY: promoter
<222> LOCATION: (1)..(1747)
<223> OTHER INFORMATION: PF3 promoter

<400> SEQUENCE: 8

```
tcgttccaac gtaccgcaat accctctata tccagtctac gggtatcccc catcgacagg     60
atggattaca agttaataga cctaagtgat acctcgaatc aagtataatg actagccatg    120
tattgtataa aaaaactttt aggtagatcg tttgagtcaa ctcatcccag agtatggcta    180
gatggatgaa aaagctcatg gatcgttagc tcatccaacg catggcttgg ctcgttgcac    240
tctcgtaata agttgagctc acattttagc tgctcatcag gctgctcaag agtcaaataa    300
gccaaggcaa gcagtggcca acacaacaac ccaacaagat aaaatcccaa ctccaccctt    360
aatccgtatg ccacctatga tggcattcca ttctatatcc aacttgactc ccatccgtcc    420
tctgttctta cgtcaccact tgtcgttcc gccaccatc aacatggtcg caacgctgcc    480
tcaacatatc atagctcaag caactccgtt catgctcttg cctatcgcct cactccatcc    540
```

```
ctatcttgct taccactcta cttcatcctc ggcagacaaa ccatgacata taacatgccg      600
atacttgact ccatctccgt cttatcgaac cgtcatggtt tcacgccaac gcgcgcaacc      660
gcattccctc gacgcaccac taggtcatgt agtaggaaga tgagatgcaa gacaaggcac      720
ctctgcccga caagtttgaa gtcaaagaac tcacataatg agaagagaca gtcgtcatca      780
tcataggtgg actttgagtt gatgtttatt ctcctagctc gctagcttaa tgagccaagc      840
ggagccagat cgagccaaat cgaactgatt cattattcag ccctattcct agagagacat      900
tcatggtaga ccttctaagt gtggtgccat ttgaatgtag acccaatcta tgtgtagagt      960
ggactaatgt gaatttgaat gttaacatgt tacgccagtc aatgtgatat catatcaatc     1020
agtagtacgg taataattca attatatgtt gtaatccctc cctgccaaaa taaattcatc     1080 tttatccccct cctatttgtc caaaaataag tttacttttta agaaaaaaat tatcaaagtt    1140
tgtgaaagta tgcgacaaat gtattggaag tagataaaaa tggaacaatt ctattaggat     1200
ttggttgggt ggagggtatt acagtctttt tgcttttgta tttatgggac aagagaaaat     1260
aaaattattt cgggacggat gtactaacat atacttcctc cgtccctaaa tatatgacgt     1320
tgttgacttt ttaaaacatt tttgaccatt cgtcttattt aaaaactttt gtgaaatatg     1380
aaaactatat atatacggaa aaatatattt aataatgaat caaatgatag aaaaaaatta     1440
ttaattactt aattttttttg aataagacga acggtcaaac atgtttaaaa aaatcaatgg    1500
tgtcaaatat ttagggacgg aggaagtact tctctcgggt ccaaaattaa ttgcaaaccc     1560
gaatccatta tccctacac caaaaataag ttttttcattt ttctcctttt agactgaccg     1620
aagctctgaa taaccgggca ggccacctat aagaatagca ttcacggggt ctgtgatccg     1680
tattcttagt gaccacccc catatcacat cctctccttc ctcttcctct gctcactcag     1740
ctctccc                                                             1747

<210> SEQ ID NO 9
<211> LENGTH: 1774
<212> TYPE: DNA
<213> ORGANISM: Oryza sativa
<220> FEATURE:
<221> NAME/KEY: promoter
<222> LOCATION: (1)..(1774)
<223> OTHER INFORMATION: PF4 promoter

<400> SEQUENCE: 9
tctggcatcg atatgctcct tccattcatc ctgagagtga gacatgtttt tttctatgtt       60
atgtgcgtgg ttttattggg taaacattgt agaaagacag tcgggcgaca tcggcttata     120
ctaaggggag aatatatgct gggaagagaa cttgaagggg actaattctg attatttatt     180
gctaaattcc aaagactagc taaataccct atatatagag ccgacacctg caactcaatc     240
taatctaatc ctacttttaa gcaacagagt atatgtaaca cgcgctgcat tggaggcatg     300
gaggcattat atctaacacc caccttgttt ccctgcatgg aggcattccc tagttttacta    360 gcttgctcag tccgttttgc tcctttcaat ctcaaaatta tatagatcct tatgtttgat     420
gttatttttg tcattaccgg tctcttcacg ttattccatt atgttaggtg ccaagaagag     480
tatgttggac cattagagtg gacatgatta gggatgcaag tggatagttc ctctactcgc     540
aaaaaaaccc gtttgctagt tcatttctta catgatagta taaatttag aagaaaaat      600 gaagtagaag tgagattagc gggctaaaga aacccgcttg catccctaga catgatccat     660
ccaccttctt attattaggt tgtaggctgc cattttttcta ccagccatttt acaagattgc    720 caaccagatt cgctctgctc tcgtagccac tttacaccac tacgcagaac tacaaatcta     780
```

| | |
|---|---|
| caggatggat tgcattgcg agcatgatgt ccccaacttt aatacaaaac tgccaatata | 840 |
| taatgagttc agcaacgtgt tagggtaaag ttttttttt ttttttgcgc agaggcagtt | 900 |
| ggaaaaaaa acctaagacc cctatcccat ataaaaaaa ccaacttgta gcttacaaac | 960 |
| ctagataata agctagaagt ttattttta tgagtaaaac aggtggcttg acagtaattc | 1020 |
| tgatggcagt gttctttga agggattgga gcatatccca ctcgcacgca aacaaagtga | 1080 |
| caaattaatg cacgattaat taagtattag cttaaaaagt ttgaaaaatg aattaatttg | 1140 |
| atttttacag taacttttgt gtaatttttt ttaaaaaag tgcaccattt aaccgtttgg | 1200 |
| gatatgtgca tgtggaaaac aagaaatatg tggttgaaac cttgagggag aacacagcca | 1260 |
| aaacaaaaaa aaatctgatg gaatcaagaa ggccaacgtt ggtgtgggcc gggcccaatg | 1320 |
| catcattttcc ttcgtacgtt gcaatctagg cccaacggac tgcccaccac cccctcgcc | 1380 |
| tgaagaatgg ggtggatcag atggcaggct cattcccagc cgtcggatcg acccgatcac | 1440 |
| cgcctgcgaa gtaaaccta agccacggcc gcctccctat ataagcccac ccactagggt | 1500 |
| ttcgcccgcc tctcctcccc cccgctagtt cccaaccagc agctgcggcg gcgcgagcac | 1560 |
| acgaagagga ggcggagcag ccggagccac ctccgccgcc gccgccacca tgggtaaggc | 1620 |
| acgcccgcaa cccgggtgct caaccttcct cctccgctta ccccatccg cgtgggggt | 1680 |
| tgtggagttc gttgtttggg ttttttgcgt gtgtgtgtgc tgatggattg atggggtgc | 1740 |
| ggtgatggct gtgcaggtat ctcgcgtgac tcca | 1774 |

<210> SEQ ID NO 10
<211> LENGTH: 1970
<212> TYPE: DNA
<213> ORGANISM: Oryza sativa
<220> FEATURE:
<221> NAME/KEY: promoter
<222> LOCATION: (1)..(1970)
<223> OTHER INFORMATION: PF5 promoter

<400> SEQUENCE: 10

| | |
|---|---|
| gctgattccg tgcacctcat cgtcgctttc ctcctcttcc aaagaaagct gtgcgaattc | 60 |
| atcggggaaa ttcctgccca tgtacttggc tgtgccatcg ccatcagtca gctgctcatt | 120 |
| tgaactcgac ctccatggcc gctcattctt ggctgctgga aaaggaacaa caagcagttc | 180 |
| agttgcacat ctacattgaa caataactga aacgctcacc cgcgttcccc tctccgtacg | 240 |
| cacctcgccg gcagctcgag agcctccgcg gtgacggctc ataccggcaa cgacccatcg | 300 |
| ccttcgtcct gaagaagagg cattttgagg agagcgaatt aggacagctg agagatcgaa | 360 |
| aaggggatcg agggagcggg tggagactgg agaggtacca ggaagggtag gggattaggg | 420 |
| cacgggagcg caggcgcagc cctagctccg gccgcagatg gagcaggcgg cgactcgcgg | 480 |
| ccatggccgc cgccgccgcc atcctgagcg tctggtgcac tgacgccgcc gcggatggtt | 540 |
| tgaagcacag ttttactcca catcccgttt atctcaccat ctcgttaata acagagtaga | 600 |
| acaactatca tcagaacttc agagggacct gtttggatag ttgtcatttg ttaatggaaa | 660 |
| cctcattaaa caatagggaa ccgtaattta tctattttc ttaaaaacac agtatataca | 720 |
| catacacaca tactcccttc gtctcataaa aaatcaacct aatactcctc catctcataa | 780 |
| aaaatcaaca tagtactaga tgtgacagat cccagtacaa cgaatctgga catccctaat | 840 |
| gtgtcacatt caatactaaa ttcactttct ttttagaaac ggagggatta cgtttatatg | 900 |
| tttatataac atgcacactc gccaaaccac atgcatccta ttattttgaa attcatgaag | 960 |
| tcaaactaca cgcgcgtttt gttatcgatt ggtacattgc ttatcattga aagaaaagta | 1020 |

| | | |
|---|---|---|
| agttccacca ccataaatct aaccaatata aatactttca ctgtgtgtaa tttatctact | 1080 |
| tttattagat taagatatgc atctattcgc tttcaagatt tcctgcagtg gtcgaaaggg | 1140 |
| gaaaacaaat cgattccttg tggttttaaa ttataataat gcaggtcaac tgatatagtt | 1200 |
| gtatgtaaaa cgggttcata tgtatggatg ctacaagtta tacattatat tcaattctaa | 1260 |
| ctttcggaaa tattatatag tggtgtagat tgatttatgt agtacggatt aattggcatt | 1320 |
| gatgtataca aaatacagtt gtatatggaa aacctaatag ttgtatatta agaattactc | 1380 |
| caatccaatt taaatcgagc tctgtataga attgtaaggg aaaaaacgct aagttaaaaa | 1440 |
| tagatataaa ctctgtaaag atgcaggtgt ccaggctaaa cttccaagat catccaataa | 1500 |
| aaggaacact tcctttact tttctcctta ggaaaaaaaa gaaaaaaaag aaagcgaaga | 1560 |
| gcaccgaaag gcgaatctaa gcgcgtccag cgtaagcatc acgcgagtcg tcggcgcgcg | 1620 |
| cggatcccg atcggacggt ccacgttgcc ccgtcgccct ataaattggt ccccccgtct | 1680 |
| cccccaccca aatcctcccc gactcctcgc agcttcctct tgttttcctt ggccgaaccc | 1740 |
| cccctcgaca cgccgtcgcc gccgagggga gagagagaga ggccgccggc cgccgctacc | 1800 |
| actgaccccc cccctcgccg gagcgccccg tcgccggtcg gtacgcgtct ctaggccccc | 1860 |
| ctctctctct cgatttgatc ggtttgatct gtggtgccct aggtttgatc tgtggattta | 1920 |
| ttttttttct tgttttgtgg gggtgattag ggtttgatcg atggcgtcca | 1970 |

<210> SEQ ID NO 11
<211> LENGTH: 1753
<212> TYPE: DNA
<213> ORGANISM: Oryza sativa
<220> FEATURE:
<221> NAME/KEY: promoter
<222> LOCATION: (1)..(1753)
<223> OTHER INFORMATION: PF6 promoter

<400> SEQUENCE: 11

| | | |
|---|---|---|
| ggaccaaccg aagtccttcc ggaggaaaga ggggaaaaat ccgagcaagc gagcaagctc | 60 |
| aggttgccac cggtgacact tcacctgagc aagctcgctc ggtctctaca ggttgcttta | 120 |
| tctgaacgca aaagcgatat tccatggaaa agctctcagg cccacggcct cattagacaa | 180 |
| ggcccaacgc tcaagtttct ttgaggcggc acatttagat aaggaaatgt ctgagggaat | 240 |
| aagatcacga aggtccctca acctaacagc gagatgagat ttttgagatc ccttacccctt | 300 |
| aaactcacat aaaccatgca atcaaagtcc tatgatagta tatatgagcg gttttgctga | 360 |
| cgtggcatcc tagtcagtca aataaaaaac aaaaaagtta tggggcctaa agtaagtga | 420 |
| gaaggaaaaa atatgagacc cacatatctt ccttttctct ttcttctcct ctcttctctt | 480 |
| tgccactgag ggggagcggc agcaggcggt gacaaggaac cggagcaggc aggcgagtgc | 540 |
| tcggcggctg acggagtgga gcggggtggt ggcagcaggc gagcgcacgt ctggagcagc | 600 |
| gtggctgtga gcgcgcgacc gacacagtgg agcggcggtg gcaagcaagt gatgttgcga | 660 |
| gtgcgactag tggagcggag cgggcagtgg tggcgcgggt gctcggcgac gccgacgccg | 720 |
| tcgcgcttgg ccacggccac gccaccaacc acctcccccct catctcctcc tcctcttctt | 780 |
| cctcttcccc aaactgcgac atctgccagg agacccacgc ctacttcttt tgcgtcgcgg | 840 |
| atcacgccct gctctgtcgg acctgcgaca gcgtcgtcca atcgccaat gccttcatct | 900 |
| ccgcccattg caggttcctt ctcaccggcg tccacgtcgc cccttgacac caccctctg | 960 |
| ctccttcgca cctggagcca ctgttcgctc gccgcgtccc aagcccctct gcacctcctg | 1020 |
| agcccggagc cgccgctcgc ccgccgacgt cgccgctccg cctgcctccg gccgcacgcc | 1080 |

| | |
|---|---|
| gccgctgctc cccttctacg gcaaatataa aaatgaagag aagaagagaa aaagtaaaag | 1140 |
| agcggcaaag ataaaaatga agagaagaag agaaaaagga aaagagaagg agattggtga | 1200 |
| ctagatcgtt gaccacatat ttttttctc acttacatgt ggatcccaca ttttattta | 1260 |
| ttttattta tgctgattag gatgtcatgt cagcaaaatc gggcaaaaat tgagtcgata | 1320 |
| ctgccatggg acctcctttg aacggtttga gtgagtttag gggtacaaat ttctggttct | 1380 |
| gtggttaagg gacctaaaaa attctcgctg ttaagttgag ggatctccgg tgaacttatt | 1440 |
| gcaatgtctg agagacaacg aagtgataga ttgggcctcc agcccacgag agtagaagtc | 1500 |
| ccagtcgcac gtttcgtcgc ctataaatac tctccccctt gggcagccac aaaccctagt | 1560 |
| cgaggagagc acccaacccc tgcgccgcca cctccgatcg tcagccatgg taaggagctc | 1620 |
| gccgcttccg gatccaccct agccgccgcg gggcggcgg ccgcttcggc gtcttcttct | 1680 |
| tctccgctca atctcccggt tagtcccttc tgattggttt cctcctttcc ctcgcagacc | 1740 |
| ttcaagcgca gga | 1753 |

```
<210> SEQ ID NO 12
<211> LENGTH: 1900
<212> TYPE: DNA
<213> ORGANISM: Oryza sativa
<220> FEATURE:
<221> NAME/KEY: promoter
<222> LOCATION: (1)..(1900)
<223> OTHER INFORMATION: PF7 promoter

<400> SEQUENCE: 12
```

| | |
|---|---|
| aactgaacag ggccttacca gaaaatctct cgctggtccg ggtattgaac tgttttcgat | 60 |
| ggttccctcc ctctctttct ctacttggca tattaacgtt tttcattcct ttacttttc | 120 |
| attacgaaaa acgattttca ttccttaac tagttattct tttaagtctc ttttaacgga | 180 |
| gaaaattgta atattgggac tgcaaacacg tgggcttcgt tgttttgaca ctccgagtgg | 240 |
| atgacaaatg ggtccatctg tatgtatgaa atataggcag tgtcattata gtaaaggtta | 300 |
| atgtttgcag tgttataatt gcaaatcccc cttttaacgt gttcttagaa ttaactagtt | 360 |
| gattggtaaa tagaaaatcc ctaaccaact taaaaaatta ttttttttaaa aaaaactgtt | 420 |
| tctaatcatt tttataacta atgagtaatt ataatttagt gctactcata aattttact | 480 |
| tttacgagta caaattttac tcataaatta atttttatgc ttcatacatt tttgcgcgca | 540 |
| tatgtatttg aaatcactac cctctaattg gtaatagcac cccctccag tcacaccaga | 600 |
| atgagtatca atccaacgtc tacaaatgat aacacaaatt gatacactaa catatgacaa | 660 |
| attcatgggg aaggctaatg cgcacgtacg cgccagcaat ttagctggca cgcgcgggcc | 720 |
| ccctctcggt tcggtgcttt tatttttatt tttcttttct tttacgtttt tgcgctcaga | 780 |
| tctaggtgct tttttttttt attttttcgc catttctttc taatttttt aatctttcgc | 840 |
| acacctcttt ataaatgtag aattgaaagt ttttaatttt gacatgaaag ttttaaaatt | 900 |
| tcgacttgaa aattttaaat tttgacttg aaagttttca aatttgcctt gaaagtttta | 960 |
| aaatttaagt tgaatgtttt caaattttgg gtgaaagttt ttaaatttga catgaaagtt | 1020 |
| ttcaaatctg agttgaaagt tttaaaatcg gggttgaaag ttttcaaatc tgggctgaaa | 1080 |
| gttttaaatt tgacttgaaa gttttcaaa tttgagatga aagttgaaa ttttcaaaa | 1140 |
| tttgagatga aagttgaaa gttttcaaaa tttgacttaa aaagattcaa gttgaaagtt | 1200 |
| ttcaaatttg aattgaaaat ttttaaattt aagttaaaag ttttaaaata tggggttgaaa | 1260 |
| gctttcagaa tttgactcag cgtataaatt tcttttcaat ttattactta aaaaaatctt | 1320 |

-continued

```
cgggaaaaaa caaatcttat cttaattatc gtcattatct ataactaatg attctaaaac    1380
taatggatta gcgtggtgga aaaaagaatc ccgaaaaaaa attttcgtcg acccgcaacc    1440
acgtatacac gtgagccgtg ggccggaagt gcgcaccgcc ggcgcgtatg cgcgaattag    1500
gaatctcgca aattcatgct tcattctgta ttgttttttt tttttttgaaa aaaggaccct    1560 tcagcccatg ctgcacgtag ctaaggccca accagccca caaagaaaaa gcagaatccc     1620
accactccgg cccacgaggc ccaccacctc aaaaccctag ccgctcccct cgcctcgtct    1680
cctctatata ggtatccctc ctcgcgccgc caccctcctt cccccttagcc ggaggccgac   1740 acgaggtaag aagcccagaa gccctagcgc cgccgcagca gcagcagcca tggtgagctc    1800
gccgccgccc gccgaccctg ttcgttccgt aggatttgtc ttcccgctcg ctgacgctgc    1860
tgtttgtatg ttgctccgca gggtatcgac ctcgttgccg                          1900
```

<210> SEQ ID NO 13
<211> LENGTH: 1886
<212> TYPE: DNA
<213> ORGANISM: Oryza sativa
<220> FEATURE:
<221> NAME/KEY: promoter
<222> LOCATION: (1)..(1886)
<223> OTHER INFORMATION: SC1 promoter

<400> SEQUENCE: 13

```
gatcacttgt ggcagccata cttgaggcat ctcgatcgtt ttcaggacgt ctctggcttg      60
acagctgagt tgagattatt caggttgatc ttttttgcttg gttcagattt cagatccgtc    120
agacttttca attctgtttt cctactcgtt ttacaggttc tgaaattgcc aaatgccgac    180
caaacgaact caacacaaga cgtgattctg ttggtattgg gaggagatag gaaggaaaaa    240
cctgtcctgc aaatgcaaaa atgcaatatg ccatattgcc ttccaatgag agtatgtcag    300
cattcaagca aacagccaaa cacagattat agttcgtccc atagaggctg gatgtggaac    360
gttagccaaa aactggattt gtaatcctaa ttttaattca tttaggcgt tccttttcaa    420 attttttaag gctgtgttta gttccttcta aaattagaag tttgggttga aattggtacg    480
atgtaactga aaatttgcgt gtgtatgtca ggttgatgtg atggaaaaag ttggaagttt    540
ggatctaaac acagcctaag tttcggcttt ttaaccaaat atcaatatac taaacgccta    600
ccgtaaaact acttttttcgt aacatcgttt ttattctatg gcttataact cgaagcctat    660
caatgtgact agtactattt tattacttaa tgaaacgtct atacattata tatatcaaaa   720
tgttataaaa ccgtaaaaaa gccatgatat caaactgaca aaataatact ctatccatcc    780
taaaatataa ggaattttat gtggatgtga cgtatcttat actttgggtg agaggaagag    840
gtactaatac cactattata ttgtactccc tccatactcg taaaagaaat cgtttaggac    900
agcgacacgg tttccaaaac acaactttga cttcttatt ctataaaagt atttattgaa     960
aagtgatata tgtatacttt tataaaatta tttttcaaga caaatctata tatataattt    1020
ttatattttc aaactcaaca acttaaaagt tatttatgat ttatattcct aagatttgat    1080
ttaagcattg tcctaaacta ctttctttat agtatggag taatatgtat tggtaacagt    1140
acagtatata cagcagtagt agtagaatat actgtactgt agggggaggt ttgggccggc    1200
agaggaatgg gccagtcgca catgccgtct gcgtgcgctt cccgcgacct agaatatcgc    1260
ccactcgctc aaccgcatat cccttcctaa taacctctcc gatccgtaaa cctcgcccat    1320
gcgccacgtc cccctagtg tcctacctcc cggaccaccc ggtcttggta gaccacgtcc    1380
acctccccaa ctaaaatatc ctccctaacc caaccacccc acgtaaccc acgtacttaa    1440
```

-continued

| | |
|---|---|
| cgcgagttac cccccgcaaa gatccaaccg cctctcgcac cgcccgcctg tccacccacg | 1500 |
| cctactgacg aacccggccc acctctccgg gccccaccat gtcgtcacca cgcaggccaa | 1560 |
| aatcggggag agcgtgtcgt ggtcccacct gtcattggct tcgtgggtgg gagcgggtca | 1620 |
| cgtgcatctc gacatgactc gaggaggtaa ccatggttat ggtaacccca ccgccttgac | 1680 |
| acccgtggtt aggggtgggg gcgcgcgatg ccgccacgtg tgacgatcgg acggctgcgg | 1740 |
| agggcatcgg ggttgggcga cccgcctatt taaccgcggg ggcctcgtct tcctcaggcc | 1800 |
| acgcagcgat ctgaagtgaa acagcaaaaa aaatcaaaca aaagaaaaa atattcccca | 1860 |
| tctgtgaaat tcgcaaaacc ctagcg | 1886 |

<210> SEQ ID NO 14
<211> LENGTH: 1978
<212> TYPE: DNA
<213> ORGANISM: Oryza sativa
<220> FEATURE:
<221> NAME/KEY: promoter
<222> LOCATION: (1)..(1978)
<223> OTHER INFORMATION: SC2 promoter

<400> SEQUENCE: 14

| | |
|---|---|
| ttacgtatag cctttccctt cggttttccc tggctgacga gtgacaaaac tgcagttgag | 60 |
| cacatgcggc aaaagaacac ccccagcgtc atcgtgccac gtggatggcc cccgcaccaa | 120 |
| atcaaacggc ccccgcgaga ggaacgccac aaccaacctc tcccctcct ctccgcagcc | 180 |
| gcacactccc gtcacgttgc ggtacggaca cccacacaca cagagacacg ctccgcctct | 240 |
| cactgatccg tgggaccacc gatccgcggc acgccagttc gggccaatca gagcccaggg | 300 |
| atccacgctg gcgatccgcg ggcagtcact caccccccgg ctcccacccc caccgccgtc | 360 |
| cgatcgtggc ggaggaaaca cacccgcgga cgatctcggc cgtccgacca cgcgggcgga | 420 |
| tataccaacc gggcggggg tgggggattc ctcgctataa ataggaggcc gccgcttggc | 480 |
| tgagcaattt ttctgcggtt tcttcttctt cttcctcctc ctcgcgctcc cccgattcga | 540 |
| agcgtgaaga gaggaacggc gcttgcgaga ggagagaggt aagcatcacg gcgaagtttc | 600 |
| cccctctctc tttcttttcg tctcgtttgc tgcgaccccg gcggggtatt gagattctcc | 660 |
| gttgaggtcg gttggttggg ggcttggggg attgggtggg ttagggcttg ggggtggggg | 720 |
| gaatttggcg atttgggggg ttttctcggg tgatctgctt gttttgcgc cgtttcgccc | 780 |
| ggtgaatgcc agccccgtgt gatttgctgg tttggttgtg gtctaatcgt ctgatattcc | 840 |
| agggctgtgt agtcctgtag ttttttgacta ggtaattgga gtgctgatgg gatttgccgt | 900 |
| tgaattttag gttgtttagc tctaatttac ctgcaacgtt ttgggaatta gggtttcttg | 960 |
| gtgaattta ggttgtttag cttaattta cctgcaacgt tttgggaatt agggtttatt | 1020 |
| ggtgatatag tggatacgca tcgtaaactt gtatttagga ttccccttgg gattttgtag | 1080 |
| gcgagtggcg gctgtatgtg attggcacga attatttact cgggtgaatt tagactagct | 1140 |
| attttattgt tgccgtgccc tttctggata tgaacggatg aatatggcgt cactgctcga | 1200 |
| tgatatcgca atgttatgat tgaaaaagca tagtagttat actgatgcca ttgtgtagta | 1260 |
| gttagttgt acctcccctg ggttgcattg caacttgcgt taatatggat actccgtaca | 1320 |
| attgtttatt gttacttgg tatagctatg ctgcattttc tatatttgtt gggttataag | 1380 |
| tttttgtcca atattttaa tgacttgtgc cagaggctct caatcctctg ttattagacc | 1440 |
| tgtaattgta aggtctattt ctccttcatt ctgtttcaat gttagtttgt ggatgtacag | 1500 |
| aaatcaagct atgattgata taatacattg ctttggcata atggcactct tattttgtt | 1560 |

-continued

| | |
|---|---|
| ttatttagga gagtgctgtg tattagtttg ttcagttaat tcaatgttgt atgttttact | 1620 |
| gtgtcgggaa cttacagatg ttctctttag gtttctatcc attagtaagt agagttgttg | 1680 |
| ctttgcttga aaccatcaat ttgaatctgt ttatagagat aggctgttat tcctgcttac | 1740 |
| tattttttat atagttactt tgccatccgt taatcaggtt aagaacaata aattgtgtcc | 1800 |
| ataatcaatg ttttcaatgg aactcacaaa attttgacag aaacatgttg ctttcttagg | 1860 |
| tcaatctcta gcatattgtt ttttttttga attgttactt gtttctgtgg tgttattaca | 1920 |
| gaaagtgctt acttccactc tagaatttta ttacattttt gtcacagcat attctgtc | 1978 |

<210> SEQ ID NO 15
<211> LENGTH: 1785
<212> TYPE: DNA
<213> ORGANISM: Oryza sativa
<220> FEATURE:
<221> NAME/KEY: promoter
<222> LOCATION: (1)..(1785)
<223> OTHER INFORMATION: SC3 promoter

<400> SEQUENCE: 15

| | |
|---|---|
| accgatgtag atgaatactt cctcggttta ggaattggga ttttatttat aagttataca | 60 |
| aagtaaatat aaaatggacg gtgcatattg attgaggtag aatattagta ctactgtttc | 120 |
| ttcttttttgg aatatactgc aaaacaacac taatgtaatg ttcggacaaa acttaaacgt | 180 |
| cattatgaat attattagct cttaataatc ggcaatagcc aataggtcag agacaaacac | 240 |
| ccatcagagg atccggattc gatcaggtga gtgccggaca aacagtatgc ggcgccatcg | 300 |
| cccgtcgccg ccgccggcta ctttctgtta gagcacgggc ctgtttagtt caagaaaaaa | 360 |
| aaattatttt tgaatgtcac attggacgtt taactagata tcgaaataga ttttggaca | 420 |
| cgaataaaaa aactaatttc ataactcgtc tggaaacagc gagacgaatc atttgagcct | 480 |
| aattaatccg tcgttagtat acgtaggtta atgtagcact tatggctaat catgaactaa | 540 |
| ttagactcaa aagattcgtc tcgtgatttc ctccctaact gtgcaattag ttttttgtttt | 600 |
| tatctatatt taatgtttca tgtatgtgtc caaagattcg atgtaatgtt tttaggaaaa | 660 |
| aaatctgtga actaaacagg gcccaagttt agccaactac taactccaaa tcacatatag | 720 |
| tcaacttaat agttaattca tacaatagtt acatactaca ctattaatac ctgatcccac | 780 |
| ctgtcataca tacactgtct cttgaagtcc atgctacagc tggctacaaa tctttagctc | 840 |
| gctgctcttc tctttcttat tttattttct taaaatatgt taccaaacga cgacacgtag | 900 |
| ccagaaacac ctcgacacga acaccccccat gtcacaccac accacaacac gatcagttca | 960 |
| actttttttt tctctttttt caaaatttca catcctttttc catcaatttt tctttacccc | 1020 |
| gcattattgc agaagcaaga aggagcaaat atgcccttt ctatttcttt cacctcccct | 1080 |
| gattctttct tgggcgacaa accacaacct gccacgtact ctactctacc cgccgcgcgt | 1140 |
| cactagctaa tgacacgtgg gcctcgccca tgcccgggcc cacacgtcag cgggacacct | 1200 |
| cacctgcctg cccctgcgct gcgccggctg cgccttctgg agaaaggta aagaaagaca | 1260 |
| ggtcacccac gcacctcgcg cttaatttat ttgtttccat ttttatttttt aattttttt | 1320 |
| cctcacgctt tctcggttcc atttggcttt attaataatt aattagactt tttcctcttg | 1380 |
| gctttataaa agagagcgct taaaccctct ccacctctcc atatccggct tccagacgct | 1440 |
| tctctcctcc tctaatctca agtctctgtc tcgtcgtcct cgcatctcca ctcgccatgg | 1500 |
| gtaattatgc tcacctccga atcgaattaa ttccccgtt tgattactgc tggtgcttcg | 1560 |
| cgtcctgatc tgattgatgt ttttttttct gattttttg gtgaattttc tggtggtgtt | 1620 |

-continued

```
tttggggacg caggcaagat taagatcgga atcaacggtg agtttgctat ctgaattact    1680
acgagtttgt gctgtgctgg gtgtggtttc gttggatttg tggtgatttg agtgggggtt    1740
ttttgtgtgt ttgggattgt gattttgttc aggtttcgga aggat                   1785
```

<210> SEQ ID NO 16
<211> LENGTH: 1886
<212> TYPE: DNA
<213> ORGANISM: Oryza sativa
<220> FEATURE:
<221> NAME/KEY: promoter
<222> LOCATION: (1)..(1886)
<223> OTHER INFORMATION: SC4 promoter

<400> SEQUENCE: 16

```
gctcgtagga caagcaggaa aagcagcgtt tgctcgtagt tgccatgaca aaatcgagat      60
aaaaaaaata acccaaaaga actgtaccta acattatact agcatgctgc atatatacaa     120
gagaagatat acataattac atatatcatt tgattaaccg ggaatggatc gaagacggcc     180
taccaaacgt gtacaagtgc attgcatctg gtcagtcagc cgcgtgcaga atgggcgaa      240 gaaactgtac aaagtgcatg gctagctaac atttactgtc acttcatcga tcgcactgag     300
tacgaaagac gagtagacga cgaccatcat tagtgacgtc cacgctaatt accctctcga     360
gtcaaacaca ggtgcaggac attagtgcgg ttaatatctt ggagtagtta attaaggcgt     420
taaatcatgt gcaaccgcac gatctctcgt tccgtccatt tgtggtgctg accacaggat     480
ggttgaagga caattgagca gtactgctca cttacatgtg agcccgagag gctatggggt     540
tcacatgtca gtgagcaata ttgcatgtac aatattgcag atgacctgca tggctgcatc     600
tggttgaagg gtagaaacac cacttttcca ctttttactc ccttgttttt catgcatatt     660
tcttcaacaa ctaaacattg tgttttctt aaaaaaattt actatagaaa agttgaattt      720
ttaaaatcat attaatctat ttttattctt ttactaatat ttaatcatgt gctaatgaac     780
tatattgttt tctgtacaga aagaagaaga gccccatcgg ttgccttaat aagccaaagc     840
aaaagataaa atttgaattt taaacttaa ttttgaagtt gatttaaaga ttttttcaa       900 catagttttt ttttcagcat cgacttttaa atcgttaaga acacatgtat aaaaagtttt     960
accaataaat tagtttttta ttatctaatg aaccaaaatg gcttattaga aaatatgagt    1020
aaccgatgag gccggaagta tccaactaat actcttgaac atagggcc tgttcatttt     1080 gatgccattt tcaaccatac cattttttt gtcaaagttg ccaaaaaata tacgtttta     1140 gtttgttacc aaatttggtc aatacataag aaatcctgcc aaaatgttgg caatattgcc    1200
atcttgttaa aattttggta ttgccaaaac ttggtaaggt ttattttggc tacaatctga    1260
acatgcctat aatagtagaa gggtttatt tgcaaatatc catctccaac ttcacgtggg     1320
actatctgag tggattaaag tggtttagaa tctaataatc gaaacccatt tgaaaaggg    1380 ttaaattatc aaatctctcc tcttgaccct cccttttctt ccatgggctt cgccggcgac    1440
tggaccctct actgtcttga atgcgcttca tagcttgttt tcatagactt cattggcgac    1500
ttgatcctag tttgttttca tgggcttac gggccactgg accctcgctt gtcttcatgg     1560
gctttatggg cctcatttc ttcagaattt tatggccttc tatacgccca ctacacctaa     1620
tcacgcgcaa aatctcactg ccggtccggc ctggcccacc cgcaacgact agtcaacacg    1680
cgctgcggcc tcgccggctt ctaggcccac gtagaaggtt cgagaacaac gaggaccgca    1740
taaaagcatc tcccacccc acgatctcgc cctctcaaaa ccctctccta accctagccg     1800
ccgccgcagc cgcagccgca gccgcgcgtc gtctcctccg ccgcgagct cctcttcccg    1860
```
ccggcgagag atcaggagca cgcaag 1886

<210> SEQ ID NO 17
<211> LENGTH: 1906
<212> TYPE: DNA
<213> ORGANISM: Oryza sativa
<220> FEATURE:
<221> NAME/KEY: promoter
<222> LOCATION: (1)..(1906)
<223> OTHER INFORMATION: SC5 promoter

<400> SEQUENCE: 17

| | | | | | |
|---|---|---|---|---|---|
| tgtgacgtgg | cagtctgaca | cgtggggtac | atgctgactc | agctgccacg | taggataaaa | 60 |
| acgggctcaa | aaccaccgaa | tgagttattg | taaccggttt | tggtaagtta | aggaaccttg | 120 |
| atatctggtt | ttgcggttcg | aggacgtttt | ttatctcggt | agcaagttga | gggaccttcg | 180 |
| gtgtactttt | ccgaacgtga | aatgggtggt | atcatgatgg | gctgttcaat | ctgtcgatat | 240 |
| ttatgggctg | aattaggctt | acaggcttag | ggcaagccga | atttcgtggg | ctattatggc | 300 |
| agcttttctc | gtgcacaaat | atggatcttt | atttggccca | ccgcgacccc | acggcataac | 360 |
| gaaacaggca | gagcccctgg | aaagatttca | gcaatacctg | ttcagacgac | gacgtctgct | 420 |
| ctgttgttcg | atttccgtcc | gcatattcgt | cgtgtgatcg | tgtccacgcc | tggagttttc | 480 |
| tggcacaggc | cgcgctcttc | tcacctcagc | ctcaggactc | aggtgatcgt | gtcaacgtcc | 540 |
| ggagctctca | ggcgatcgtg | tctcacttca | caggttgaca | ggtcggcgca | ttcgatgccg | 600 |
| ttccaaacgc | agaaaattta | gagaaacatc | tcgggacaga | gcggcgctcc | cacgcgtgga | 660 |
| atcccgcaga | tgtaaaactt | cgttacaatt | tacagtgttc | gcaacatcaa | gaaacgacat | 720 |
| tttttcattc | gaaaatgctg | caaatctgca | actggcaatc | tctagacaaa | tcctttccct | 780 |
| ttcgatgccg | aagcagaatt | gaagtttgag | aatgttcttc | gtctagaccg | agcagtcagt | 840 |
| gatctgcaag | cgcgaggcgt | tcacagatcg | tctcgacgac | ctccctcccc | tgggacgcgt | 900 |
| tctgcctgaa | cctctccgcg | caccgccgct | ccaccatctc | ggccgccag | gccgccacgg | 960 |
| cagcgagcgg | cgcgcaccga | atgctcgtct | cctgccggaa | cagcgtccac | tcgtcgggcc | 1020 |
| gctccgggtg | cgggcggtag | ctgcaggtct | cctcgacgtg | caccagcgcc | cggaggttgg | 1080 |
| cgttgcggga | gatcacccgc | atggcccgtg | cgggcccgtc | cacggtggtg | tgctcgacgc | 1140 |
| agagcaccac | gtcggcggcg | gcgacgaggc | cgcggaggag | gagcgggagc | ggcggcgccc | 1200 |
| gccccgcgat | ggcgcgcacg | gcgtcgatgc | gccccgatcc | agcgtcgacg | cggcgggaca | 1260 |
| gcgtgtgcac | ctcgaggatg | tgcgacagcg | gcgccgcccg | cgcgtccgcg | tccgtgaact | 1320 |
| tgcgccacgc | cgccgcggtc | acccggtgcc | acgggtggcg | gtacacgtgc | tcctgcgtgt | 1380 |
| acgagaccac | catgccggcc | ggccggccgc | cgcttgcctg | tgcgcgcgcg | cgtcgcgtcg | 1440 |
| cgccgagatc | gagcgaggct | agcgagagcg | atttcgacag | caactgcagc | gaaataatgg | 1500 |
| gaatatgagt | gtgtgtggac | tccggactcc | ggaggaagag | aggaatattc | gagttccacg | 1560 |
| gggaattaaa | cccattattt | tgggctcaat | ttgcttggac | tgcaaagcta | ccagacctgc | 1620 |
| agcccagcgc | atctacagat | gggccaaatt | ttgacatact | tcttagtggg | cctaagaatt | 1680 |
| catgaattgg | ggccggccta | aggccagcag | cccagtgagt | catcacctcg | cgacctaatg | 1740 |
| tctcgatcca | acggcgaaga | tcaaaaccct | aacctgcgcc | atcgtcgact | atattaaaag | 1800 |
| cccactcctc | cccgcgccgc | cgcccttctc | tcgagcaagc | acccaaaccc | tcccctctac | 1860 |
| cccgccgccg | ccgccgagga | aggggcaaga | ggaagccggc | gaagat | | 1906 |

<210> SEQ ID NO 18
<211> LENGTH: 1842
<212> TYPE: DNA
<213> ORGANISM: Oryza sativa
<220> FEATURE:
<221> NAME/KEY: promoter
<222> LOCATION: (1)..(1842)
<223> OTHER INFORMATION: SC6 promoter

<400> SEQUENCE: 18

```
gtgcactcaa ggtcctatgg tagtatatat gggtgatttc gctgacgtgg catcctagtc      60
agcaaaaaaa aattaaaaag tatatggggc ccacatgtca gctgcacatt ttattttctt     120
ctccttctcc tctctcttct catcttcagt gaaggaggcc agcggtgggc ggagcggcgg     180
cggtcgagca cagcgacggg tagagcagcg gtgggcaagc gcgtcagcgg agcggcgggg     240
ggctacgggc gtgcacgacg gctagtagag cagcgggggg cgagcgcggc ggcggtgaac     300
tacatctcca agagggggggg tggaggaggc caccggtgcc gtgtggtgca cggtcacccc     360
gaccgcaacc cgtccttgtc atggtcctcc ccttcatcga caagcctcct gaagtcgagg     420
tccatctcga ggagctcccc cgtgctcagc caccaccacc gcccgtgccc ccgcgagtgg     480
ctcatgatgc taggagcggc accaccagcg ggagaagggg aagaggcaga ggaggagatg     540
atttcttggt cactgattgc ctccctcgca tgcaagctag gcgagctcgg acgggctcgc     600
cggccgcctc cccttccctc ccaatctgct tcgcccgcgg cctgcatcca cgctcgccca     660
tcgccggcct ccctcattga agatgagaag agataagaga gagaaagag aaggagaaga      720
atagagaatg tgcagctgac atgtgggccc catgtacttt tttattttttt ttgctgacta     780
tgatgccacg tcagcgaaac cacccatata tatactgtca taggaccttg agtgcgcggt     840
ttgtgtgagt ttatgggtac acatttatgg ttttgtggtt aagggacctc aaaaaatctc     900
gttgttaagt tgagggacct ccggtgaact tattcatcaa aaaagatca ctaggtccaa      960
caaatctgac agacagacct tgcaaaggcc cattaaagca caattaactg ggcctgaaaa    1020
gcccagcccg tccactctga cgattctacc cctctaaccc tacaccggcc agcgactata    1080
taaaagcgga cccgtctcga gccgctaggg ttcttcgatt tctccctcgc gccgccgcct    1140
cctcctcacc ctccccgccc caggcgcacc ctacgcttgg agctcgtccg atccgctcgg    1200
cgcccgccat ggtaaacgcg cgaagctctg aatccatcct ctgttcctcg cggtctcgcg    1260
tgcgtgccgt gctgcttgct ggttgatgct aatctcctca ctcgcgtttc gcctgtttgt    1320
tgttgcagat catcccgaag aagaaccgca atgagatctg caagtacctc ttccaaggtc    1380
agtggttctt ggtccctatt tgcacctcgt aatcgtacta gaggcgtaga gccgccgcca    1440
tgtttagtgg agattgttgt tttaggtttg caaaacgagg agattcgtgt tgctccgtac    1500
aggagcacgg ttcttagtgc aggaactgcc ctcttgttaa aaggagaagc ttggtttaga    1560
tgtaggattt gatatgctag tgataatttt tcattctagg aacccaatga actattggtt    1620
atatactagc gaaatctgtg cacccatgaa catcaactta aattgattgt ttcggtcctg    1680
gtgttgtgaa aatctgtgtg taaaaatttc aagaaaaatg atatcgctgt tggtgtatgt    1740
cagtacagcg ttcgcatgcc aagaggctca aactgaaagt gattgtaggt gctggtttta    1800
acttggtgta tgctgttgtt gcagagggag tgctgtatgc ca                       1842
```

<210> SEQ ID NO 19
<211> LENGTH: 1876
<212> TYPE: DNA
<213> ORGANISM: Oryza sativa

```
<220> FEATURE:
<221> NAME/KEY: promoter
<222> LOCATION: (1)..(1876)
<223> OTHER INFORMATION: SC7 promoter

<400> SEQUENCE: 19
gtcgaactca ccgtgcacta tatcaaccgc cgaagaaata aattcttcgt caccatccga      60
tgaaaactca tccaatagca tttggaggag ggtgcttcga cgactcatct cctcttttg     120 tttgccacgg tgttggagcg tttaccacag ggatgaagtg caatggaggg aactgatggc    180
aggaatagaa caataatcaa tctgcaaaat taattatcag atcaaactta atattttcca    240
acaatatata tccacatcaa aatactgaca tagagattga ctacggcaca agagattaat    300
gggatttgct aaggattacc tccttgatga cacgaattgc tacgacatct ccttggtgtt    360
ccgtttttta acaaatcgca gcagtcagga cactggttgg ctggctggtg atgatggcgc    420
taggtcacgg cggcgcaagt gtggggagga agaagtcgat cggcgctggt gcggagggga    480
gaagacgtgc gcaagtaccg aactgggccc caccttgctt atgtggcaaa ctaacaaatg    540
atagggaatt gattttggg cttctcttgg aggaggggt cattgttggg cccaatttt      600 attttggtat tcctaattca gattttttgg gaatcaaata ttgggtgatt gttgggcatg    660
ctctaagtga tttgtttggt tgggagacat ggaaaattta gtgggatagg gatggtgaat    720
tgaggaagga actccctcct tttcaatacc tgggtagggg caggtaattg ggagggaatt    780
cctcctttac tttttctaag caaatctgag ccatctgttt ttattaatga cttaatctcc    840
aactaaactc cctatcaatt tccattacct ctaccaaaca agatattgag attaaaaatc    900
aaattcccat cttaatctca ttatcaattc cctcgtgtaa actcccaatc tccttccctc    960
gagttaccaa acaagccgtt agatcactaa gaatacgtat ataaaagttt tattcacaaa   1020 tttttttccat ttacaaatat gccgatgggt cctggtgatt tacttaacaa atgtttgatt  1080
agatcttcag ttttatatac aaattcgttt tgtctaaaca gataaaattg acttattaat   1140
cttgggaagg ccgttactca ctctagactt tactcctcct tatctttttt tttcttgaac   1200
gaacatttca tttcttatat ttttgcatag ttttttttaag gtagttatag acaaaagtga   1260
taatgattgg gcttctaaat aatgggtaag acttgtctcc aacaagtgac ccataagggc    1320
acctaaatct aaaatggggtt tccgatagta ttatttcagc ctccaacaga gtacctatac  1380
agaagaccta ttttacgtgc tataagaggc ataacctaaa tctgagtatc ctctctcctg    1440
aagacctatt tgcagtaagg gttctctttt aggccttatt gttggagaag accaaaaata    1500
ggtattgaac tcttttactg tagcgctatg caaacgtgaa atgagtcttg tattttgggt    1560
ttcattgttg gagatagcct aaccaccacg cgccggaagc caaacccagt tctccccgtt   1620
cccgcctaca ttttcgccac gtcagcgatc cgcaccgaaa tgcatcgcag ccgtttacgg    1680
aaacagcatc gaacgtcaca cgttcgtcca cgttatcgat ccgtggggaa accactccac    1740
caatcagcgc ccacctcaag ttcgctataa agtcgtcgcc ccgtcccca ttctcttccc    1800 cacatcgcag tcttgcaaac acacgcagca aaatccacac cgcttcccct ccccgagaag    1860
aagagagcag catcca                                                    1876

<210> SEQ ID NO 20
<211> LENGTH: 1930
<212> TYPE: DNA
<213> ORGANISM: Oryza sativa
<220> FEATURE:
<221> NAME/KEY: promoter
<222> LOCATION: (1)..(1930)
<223> OTHER INFORMATION: SC8 promoter
```

<400> SEQUENCE: 20

```
aaaaaacttg actgcccaaa atctgctcca caggcattgg ccttgcaatt ggatatgttg      60
cgtttgtggt tgtgcctttg aagatacaaa tcatttgttc agtgattgtg tgtttgtcag     120
acaagtgtag accctaattt gtcaattcca aaacttgact tcggtcggaa taaatcctgt     180
cctggatgtg tcaacatggt ggtctggaac caaatttgca ggctctaaga aggatgtgca     240
gttggtcagg gaaactcttc taactacttg ctggaatatt tggttagaaa gaaatagaag     300
aattttccaa aactcttcct gttcagagat tgaagtagct tatttatca agcaagctat      360
tgatatgcgc tgcttggcct ttaaacccca ataatttttt ttagcttttc ctgtagctgt     420
attatctttt ccattccttg gcttgtaacc tctgaacctc tgtgctactt tgtaatttct     480
ctctcctaat gttaaatttt ggcagatctc ctaccgtcgt tctcctcaaa aaataatat      540
aattataccca tggaaagaaa aaaactgaa ggacacgtta gagatcgact caaatatcag     600
gggagtgcaa gggattttct cttgttatta gaataatttt agtggcgcat ggcataaacg     660
aatgtgaagg caattatctt ggttgcagca tcgagctaag agatcaacac gagcagctga     720
agcgacaacg actacatggt cgcgaactca agagcagcag tgagggaagc caaggcattg     780
gcacttggca gaacaaagct gggtcgagga ggatattgat atcggggttg agtagattaa     840
attagacttg aaaaatatggg aattgccaat gagttgatat atttgtcaac aaacatagtt    900
taatatattg taggccaaag acaagctatg tcaaaatcaa ctttctgcta atgtttaact    960
gagttttttaa tttcatttg aaaagtgatt cacatttgat gatgtctcaa gtgccttag    1020
catcaagctt tccattctat ttcatttgta ctccacctgt tccaagattc tatttgtcac   1080
aaaatattca tatttaaact ttgaccattt gttttttctt taaaattaaa tacttataat   1140
atatcatatt attagggcgt gttgaagcct aacctaagca ttaatatttg ttcatcatag   1200
tctaatcact taaaaatagc catgatcgaa gttaaaacaa cgcttgtcaa acaaataaaa   1260
aagtatttgg aagcggatat agttattgcc tagcccggtc tagaacctca cagaaaatca   1320
cacctagtat atcttggaaa gccaaataaa gtggctaaat gaattaatcg attttttcacc   1380
caagaatttt atcagaacct tattgacttg aattttacaa caataaagag ttcagcatga   1440
cgcctttgca taatagcata atagtaccac ataaaaacca tggtagaatc tattatagaa   1500
ttgcgcattt atcgtgaaac attttgaaat caatatttgg tcaaaatttc ttatgtatac   1560
attaaaactt aaaaaaaatcc agtactctaa aaaaaattgt aattctcgat acacaaaaat   1620
cgtcgcgtcc ctatgaccca tgggccccttc cacaatttcg ctcacgcgcg agaaaatccc   1680
gccccgcgct cgtctcttcg cgcccagata tttcaccacg tcagcaatcc gcgccgaaac   1740
gcatcccacc cgttcaccgc aaacagcggc gaacgacacg aatccttcca cgtcatcgat   1800
ccgcgccgca tgctttccac caatcagggc gcacatcccc tcttctataa aaccaatcgg   1860
ccccgtctcc tcctcttccc aaccgcaaat cttgcgatcc acacacagca aagaaccac   1920
caccgtttcc                                                            1930
```

<210> SEQ ID NO 21
<211> LENGTH: 20
<212> TYPE: DNA
<213> ORGANISM: Artificial Sequence
<220> FEATURE:
<223> OTHER INFORMATION: APX forward primer

<400> SEQUENCE: 21

```
gacctctaga ccgccgtatt                                                   20
```

<210> SEQ ID NO 22
<211> LENGTH: 20
<212> TYPE: DNA
<213> ORGANISM: Artificial Sequence
<220> FEATURE:
<223> OTHER INFORMATION: APX reverse primer

<400> SEQUENCE: 22
gccaaccact cgcaatccaa         20

<210> SEQ ID NO 23
<211> LENGTH: 20
<212> TYPE: DNA
<213> ORGANISM: Artificial Sequence
<220> FEATURE:
<223> OTHER INFORMATION: SCP1 forward primer

<400> SEQUENCE: 23
tcgctgccta cgccaacatc         20

<210> SEQ ID NO 24
<211> LENGTH: 20
<212> TYPE: DNA
<213> ORGANISM: Artificial Sequence
<220> FEATURE:
<223> OTHER INFORMATION: SCP1 reverse primer

<400> SEQUENCE: 24
tcgccgaact agcaggtgag         20

<210> SEQ ID NO 25
<211> LENGTH: 20
<212> TYPE: DNA
<213> ORGANISM: Artificial Sequence
<220> FEATURE:
<223> OTHER INFORMATION: PGD1 forward primer

<400> SEQUENCE: 25
ccgtgagcta gcgaggatct         20

<210> SEQ ID NO 26
<211> LENGTH: 20
<212> TYPE: DNA
<213> ORGANISM: Artificial Sequence
<220> FEATURE:
<223> OTHER INFORMATION: PGD1 reverse primer

<400> SEQUENCE: 26
ccggtaggag tcgaagtacg         20

<210> SEQ ID NO 27
<211> LENGTH: 20
<212> TYPE: DNA
<213> ORGANISM: Artificial Sequence
<220> FEATURE:
<223> OTHER INFORMATION: R1G1 forward primer

<400> SEQUENCE: 27
cttctcgatt gccgtgtgct         20

<210> SEQ ID NO 28
<211> LENGTH: 20
<212> TYPE: DNA
<213> ORGANISM: Artificial Sequence
<220> FEATURE:
<223> OTHER INFORMATION: R1G1 reverse primer

<210> SEQ ID NO 28

[...continuing from previous]

<400> SEQUENCE: 28
gcaagtctca agctctcaat         20

<210> SEQ ID NO 29
<211> LENGTH: 20
<212> TYPE: DNA
<213> ORGANISM: Artificial Sequence
<220> FEATURE:
<223> OTHER INFORMATION: EIF5 forward primer

<400> SEQUENCE: 29
gatctgcgct ctgaaggata         20

<210> SEQ ID NO 30
<211> LENGTH: 20
<212> TYPE: DNA
<213> ORGANISM: Artificial Sequence
<220> FEATURE:
<223> OTHER INFORMATION: EIF5 reverse primer

<400> SEQUENCE: 30
aaccgcaaga tggaacaacg         20

<210> SEQ ID NO 31
<211> LENGTH: 20
<212> TYPE: DNA
<213> ORGANISM: Artificial Sequence
<220> FEATURE:
<223> OTHER INFORMATION: PF1 forward primer

<400> SEQUENCE: 31
ggtctcttcg ccaagctcct         20

<210> SEQ ID NO 32
<211> LENGTH: 20
<212> TYPE: DNA
<213> ORGANISM: Artificial Sequence
<220> FEATURE:
<223> OTHER INFORMATION: PF1 reverse primer

<400> SEQUENCE: 32
cgcctcctcc ttcttctcct         20

<210> SEQ ID NO 33
<211> LENGTH: 20
<212> TYPE: DNA
<213> ORGANISM: Artificial Sequence
<220> FEATURE:
<223> OTHER INFORMATION: PF2 forward primer

<400> SEQUENCE: 33
agctcaagga ccttcagttc         20

<210> SEQ ID NO 34
<211> LENGTH: 20
<212> TYPE: DNA
<213> ORGANISM: Artificial Sequence
<220> FEATURE:
<223> OTHER INFORMATION: PF2 reverse primer

<400> SEQUENCE: 34
acggcggact gcatagataa         20

<210> SEQ ID NO 35
<211> LENGTH: 20

-continued

```
<212> TYPE: DNA
<213> ORGANISM: Artificial Sequence
<220> FEATURE:
<223> OTHER INFORMATION: PF3 forward primer

<400> SEQUENCE: 35
ggtcactcca tcgtcagaat                                                    20

<210> SEQ ID NO 36
<211> LENGTH: 20
<212> TYPE: DNA
<213> ORGANISM: Artificial Sequence
<220> FEATURE:
<223> OTHER INFORMATION: PF3 reverse primer

<400> SEQUENCE: 36
acttgctcca cactgatcac                                                    20

<210> SEQ ID NO 37
<211> LENGTH: 20
<212> TYPE: DNA
<213> ORGANISM: Artificial Sequence
<220> FEATURE:
<223> OTHER INFORMATION: PF4 forward primer

<400> SEQUENCE: 37
caatgtggca gagctgatgg                                                    20

<210> SEQ ID NO 38
<211> LENGTH: 20
<212> TYPE: DNA
<213> ORGANISM: Artificial Sequence
<220> FEATURE:
<223> OTHER INFORMATION: PF4 reverse primer

<400> SEQUENCE: 38
ggtctgtagg cacgacatag                                                    20

<210> SEQ ID NO 39
<211> LENGTH: 20
<212> TYPE: DNA
<213> ORGANISM: Artificial Sequence
<220> FEATURE:
<223> OTHER INFORMATION: PF5 forward primer

<400> SEQUENCE: 39
ggagtcctgc acttaccata                                                    20

<210> SEQ ID NO 40
<211> LENGTH: 20
<212> TYPE: DNA
<213> ORGANISM: Artificial Sequence
<220> FEATURE:
<223> OTHER INFORMATION: PF5 reverse primer

<400> SEQUENCE: 40
ccatggcgta cttctgtgtc                                                    20

<210> SEQ ID NO 41
<211> LENGTH: 18
<212> TYPE: DNA
<213> ORGANISM: Artificial Sequence
<220> FEATURE:
<223> OTHER INFORMATION: PF6 forward primer

<400> SEQUENCE: 41
gaagctgtac gccaaggt                                                      18
```

<210> SEQ ID NO 42
<211> LENGTH: 20
<212> TYPE: DNA
<213> ORGANISM: Artificial Sequence
<220> FEATURE:
<223> OTHER INFORMATION: PF6 reverse primer

<400> SEQUENCE: 42
taggtgcgag caacattagg                                          20

<210> SEQ ID NO 43
<211> LENGTH: 20
<212> TYPE: DNA
<213> ORGANISM: Artificial Sequence
<220> FEATURE:
<223> OTHER INFORMATION: PF7 forward primer

<400> SEQUENCE: 43
cacagccaca cgaagccata                                          20

<210> SEQ ID NO 44
<211> LENGTH: 20
<212> TYPE: DNA
<213> ORGANISM: Artificial Sequence
<220> FEATURE:
<223> OTHER INFORMATION: PF7 reverse primer

<400> SEQUENCE: 44
gcacaatgcc gatcgcaaca                                          20

<210> SEQ ID NO 45
<211> LENGTH: 20
<212> TYPE: DNA
<213> ORGANISM: Artificial Sequence
<220> FEATURE:
<223> OTHER INFORMATION: SC1 forward primer

<400> SEQUENCE: 45
agcaccttcc accgcgtgat                                          20

<210> SEQ ID NO 46
<211> LENGTH: 20
<212> TYPE: DNA
<213> ORGANISM: Artificial Sequence
<220> FEATURE:
<223> OTHER INFORMATION: SC1 reverse primer

<400> SEQUENCE: 46
ttcgccatgg acaggatgcc                                          20

<210> SEQ ID NO 47
<211> LENGTH: 20
<212> TYPE: DNA
<213> ORGANISM: Artificial Sequence
<220> FEATURE:
<223> OTHER INFORMATION: SC2 forward primer

<400> SEQUENCE: 47
ctgcggaggc ataccttgtt                                          20

<210> SEQ ID NO 48
<211> LENGTH: 20
<212> TYPE: DNA
<213> ORGANISM: Artificial Sequence
<220> FEATURE:
<223> OTHER INFORMATION: SC2 reverse primer

```
<400> SEQUENCE: 48
acactacgac gcatgcttca                                                20

<210> SEQ ID NO 49
<211> LENGTH: 20
<212> TYPE: DNA
<213> ORGANISM: Artificial Sequence
<220> FEATURE:
<223> OTHER INFORMATION: SC3 forward primer

<400> SEQUENCE: 49
aacgtggacg gtgttcatca                                                20

<210> SEQ ID NO 50
<211> LENGTH: 20
<212> TYPE: DNA
<213> ORGANISM: Artificial Sequence
<220> FEATURE:
<223> OTHER INFORMATION: SC3 reverse primer

<400> SEQUENCE: 50
caactgcact ggacggctta                                                20

<210> SEQ ID NO 51
<211> LENGTH: 20
<212> TYPE: DNA
<213> ORGANISM: Artificial Sequence
<220> FEATURE:
<223> OTHER INFORMATION: SC4 forward primer

<400> SEQUENCE: 51
aacaccttcg gcaccaggat                                                20

<210> SEQ ID NO 52
<211> LENGTH: 20
<212> TYPE: DNA
<213> ORGANISM: Artificial Sequence
<220> FEATURE:
<223> OTHER INFORMATION: SC4 reverse primer

<400> SEQUENCE: 52
aagcgaacag cagcagtcag                                                20

<210> SEQ ID NO 53
<211> LENGTH: 18
<212> TYPE: DNA
<213> ORGANISM: Artificial Sequence
<220> FEATURE:
<223> OTHER INFORMATION: SC5 forward primer

<400> SEQUENCE: 53
catcttgcgg tcggagaa                                                  18

<210> SEQ ID NO 54
<211> LENGTH: 20
<212> TYPE: DNA
<213> ORGANISM: Artificial Sequence
<220> FEATURE:
<223> OTHER INFORMATION: SC5 reverse primer

<400> SEQUENCE: 54
tacgcatcct ctgtgatggt                                                20

<210> SEQ ID NO 55
<211> LENGTH: 20
```

```
<212> TYPE: DNA
<213> ORGANISM: Artificial Sequence
<220> FEATURE:
<223> OTHER INFORMATION: SC6 forward primer

<400> SEQUENCE: 55
catttggttc tggcccacct                                              20

<210> SEQ ID NO 56
<211> LENGTH: 20
<212> TYPE: DNA
<213> ORGANISM: Artificial Sequence
<220> FEATURE:
<223> OTHER INFORMATION: SC6 reverse primer

<400> SEQUENCE: 56
gtctgccacc agagctccta                                              20

<210> SEQ ID NO 57
<211> LENGTH: 18
<212> TYPE: DNA
<213> ORGANISM: Artificial Sequence
<220> FEATURE:
<223> OTHER INFORMATION: SC7 forward primer

<400> SEQUENCE: 57
cgtcaccaag ttcacttc                                                18

<210> SEQ ID NO 58
<211> LENGTH: 22
<212> TYPE: DNA
<213> ORGANISM: Artificial Sequence
<220> FEATURE:
<223> OTHER INFORMATION: SC7 reverse primer

<400> SEQUENCE: 58
ccacctaatt cttcttacag tc                                           22

<210> SEQ ID NO 59
<211> LENGTH: 18
<212> TYPE: DNA
<213> ORGANISM: Artificial Sequence
<220> FEATURE:
<223> OTHER INFORMATION: SC8 forward primer

<400> SEQUENCE: 59
caaggctgtg accaagtt                                                18

<210> SEQ ID NO 60
<211> LENGTH: 20
<212> TYPE: DNA
<213> ORGANISM: Artificial Sequence
<220> FEATURE:
<223> OTHER INFORMATION: SC8 reverse primer

<400> SEQUENCE: 60
ctacagcaca gtaccatacc                                              20

<210> SEQ ID NO 61
<211> LENGTH: 20
<212> TYPE: DNA
<213> ORGANISM: Artificial Sequence
<220> FEATURE:
<223> OTHER INFORMATION: OsCc1 forward primer

<400> SEQUENCE: 61
actctacggc caacaagaac                                              20
```

```
<210> SEQ ID NO 62
<211> LENGTH: 20
<212> TYPE: DNA
<213> ORGANISM: Artificial Sequence
<220> FEATURE:
<223> OTHER INFORMATION: OsCc1 reverse primer

<400> SEQUENCE: 62
ctcctgtggc ttcttcaacc                                              20

<210> SEQ ID NO 63
<211> LENGTH: 20
<212> TYPE: DNA
<213> ORGANISM: Artificial Sequence
<220> FEATURE:
<223> OTHER INFORMATION: Act1 forward primer

<400> SEQUENCE: 63
atggtgtcag ccacactgtc                                              20

<210> SEQ ID NO 64
<211> LENGTH: 20
<212> TYPE: DNA
<213> ORGANISM: Artificial Sequence
<220> FEATURE:
<223> OTHER INFORMATION: Act1 reverse primer

<400> SEQUENCE: 64
taaccacgct ccgtcaggat                                              20

<210> SEQ ID NO 65
<211> LENGTH: 20
<212> TYPE: DNA
<213> ORGANISM: Artificial Sequence
<220> FEATURE:
<223> OTHER INFORMATION: OsUbi forward primer

<400> SEQUENCE: 65
atggagctgc tgctgttcta                                              20

<210> SEQ ID NO 66
<211> LENGTH: 20
<212> TYPE: DNA
<213> ORGANISM: Artificial Sequence
<220> FEATURE:
<223> OTHER INFORMATION: OsUbi reverse primer

<400> SEQUENCE: 66
ttcttccatg ctgctctacc                                              20

<210> SEQ ID NO 67
<211> LENGTH: 32
<212> TYPE: DNA
<213> ORGANISM: Artificial Sequence
<220> FEATURE:
<223> OTHER INFORMATION: APX promoter forward primer

<400> SEQUENCE: 67
aaaaagcagg ctgtaaggtg acatggcata tc                                32

<210> SEQ ID NO 68
<211> LENGTH: 32
<212> TYPE: DNA
<213> ORGANISM: Artificial Sequence
<220> FEATURE:
<223> OTHER INFORMATION: APX promoter reverse primer
```

```
<400> SEQUENCE: 68
agaaagctgg gtccaatccg aatcaatcaa tc                                      32

<210> SEQ ID NO 69
<211> LENGTH: 32
<212> TYPE: DNA
<213> ORGANISM: Artificial Sequence
<220> FEATURE:
<223> OTHER INFORMATION: SCP1 promoter forward primer

<400> SEQUENCE: 69
aaaaagcagg ctttgacttt ttctgcgaag aa                                      32

<210> SEQ ID NO 70
<211> LENGTH: 32
<212> TYPE: DNA
<213> ORGANISM: Artificial Sequence
<220> FEATURE:
<223> OTHER INFORMATION: SCP1 promoter reverse primer

<400> SEQUENCE: 70
agaaagctgg gttaactctt gccggaaaag aa                                      32

<210> SEQ ID NO 71
<211> LENGTH: 32
<212> TYPE: DNA
<213> ORGANISM: Artificial Sequence
<220> FEATURE:
<223> OTHER INFORMATION: PGD1 promote forward primer

<400> SEQUENCE: 71
aaaaagcagg cttagatatg ccgaacatga cc                                      32

<210> SEQ ID NO 72
<211> LENGTH: 32
<212> TYPE: DNA
<213> ORGANISM: Artificial Sequence
<220> FEATURE:
<223> OTHER INFORMATION: PGD1 promote reverse primer

<400> SEQUENCE: 72
agaaagctgg gtgcagatag atgcaccaaa tg                                      32

<210> SEQ ID NO 73
<211> LENGTH: 32
<212> TYPE: DNA
<213> ORGANISM: Artificial Sequence
<220> FEATURE:
<223> OTHER INFORMATION: R1G1 promoter forward primer

<400> SEQUENCE: 73
aaaaagcagg ctatagctgt tgtactgatg tc                                      32

<210> SEQ ID NO 74
<211> LENGTH: 32
<212> TYPE: DNA
<213> ORGANISM: Artificial Sequence
<220> FEATURE:
<223> OTHER INFORMATION: R1G1  promoter reverse primer

<400> SEQUENCE: 74
agaaagctgg gttctctcgc agtattacca ac                                      32

<210> SEQ ID NO 75
<211> LENGTH: 32
```

```
<212> TYPE: DNA
<213> ORGANISM: Artificial Sequence
<220> FEATURE:
<223> OTHER INFORMATION: EIF-5A promoter forward primer

<400> SEQUENCE: 75
aaaaagcagg ctttgttcca cctcatcatt aa                                32

<210> SEQ ID NO 76
<211> LENGTH: 32
<212> TYPE: DNA
<213> ORGANISM: Artificial Sequence
<220> FEATURE:
<223> OTHER INFORMATION: EIF-5A reverse primer

<400> SEQUENCE: 76
agaaagctgg gtcaacctgc caccaacaac aa                                32

<210> SEQ ID NO 77
<211> LENGTH: 32
<212> TYPE: DNA
<213> ORGANISM: Artificial Sequence
<220> FEATURE:
<223> OTHER INFORMATION: PF1 promoter forward primer

<400> SEQUENCE: 77
aaaaagcagg ctctcggtga agatagagaa gg                                32

<210> SEQ ID NO 78
<211> LENGTH: 32
<212> TYPE: DNA
<213> ORGANISM: Artificial Sequence
<220> FEATURE:
<223> OTHER INFORMATION: PF1 promoter reverse primer

<400> SEQUENCE: 78
agaaagctgg gtctcgagct gatctacgaa ct                                32

<210> SEQ ID NO 79
<211> LENGTH: 32
<212> TYPE: DNA
<213> ORGANISM: Artificial Sequence
<220> FEATURE:
<223> OTHER INFORMATION: PF2 promoter forward primer

<400> SEQUENCE: 79
aaaaagcagg ctcaacggga cactgtcgat tc                                32

<210> SEQ ID NO 80
<211> LENGTH: 32
<212> TYPE: DNA
<213> ORGANISM: Artificial Sequence
<220> FEATURE:
<223> OTHER INFORMATION: PF2 promoter reverse primer

<400> SEQUENCE: 80
agaaagctgg gtggtgccgc ctcttcaaat ct                                32

<210> SEQ ID NO 81
<211> LENGTH: 32
<212> TYPE: DNA
<213> ORGANISM: Artificial Sequence
<220> FEATURE:
<223> OTHER INFORMATION: PF3 promoter forward primer

<400> SEQUENCE: 81
aaaaagcagg cttcgttcca acgtaccgca at                                32
```

<210> SEQ ID NO 82
<211> LENGTH: 32
<212> TYPE: DNA
<213> ORGANISM: Artificial Sequence
<220> FEATURE:
<223> OTHER INFORMATION: PF3 promoter reverse primer

<400> SEQUENCE: 82
agaaagctgg gtgggagagc tgagtgagca ga                          32

<210> SEQ ID NO 83
<211> LENGTH: 32
<212> TYPE: DNA
<213> ORGANISM: Artificial Sequence
<220> FEATURE:
<223> OTHER INFORMATION: PF4 promoter forward primer

<400> SEQUENCE: 83
aaaaagcagg cttctggcat cgatatgctc ct                          32

<210> SEQ ID NO 84
<211> LENGTH: 32
<212> TYPE: DNA
<213> ORGANISM: Artificial Sequence
<220> FEATURE:
<223> OTHER INFORMATION: PF4 promoter reverse primer

<400> SEQUENCE: 84
agaaagctgg gttggagtca cgcgagatac ct                          32

<210> SEQ ID NO 85
<211> LENGTH: 32
<212> TYPE: DNA
<213> ORGANISM: Artificial Sequence
<220> FEATURE:
<223> OTHER INFORMATION: PF5 promoter forward primer

<400> SEQUENCE: 85
aaaaagcagg ctgctgattc cgtgcacctc at                          32

<210> SEQ ID NO 86
<211> LENGTH: 32
<212> TYPE: DNA
<213> ORGANISM: Artificial Sequence
<220> FEATURE:
<223> OTHER INFORMATION: PF5 promoter reverse primer

<400> SEQUENCE: 86
agaaagctgg gtgatcctct tggacgccat cg                          32

<210> SEQ ID NO 87
<211> LENGTH: 32
<212> TYPE: DNA
<213> ORGANISM: Artificial Sequence
<220> FEATURE:
<223> OTHER INFORMATION: PF6 promoter forward primer

<400> SEQUENCE: 87
aaaaagcagg ctggaccaac cgaagtcctt cc                          32

<210> SEQ ID NO 88
<211> LENGTH: 30
<212> TYPE: DNA
<213> ORGANISM: Artificial Sequence
<220> FEATURE:
<223> OTHER INFORMATION: PF6 promoter reverse primer -continued

```
<400> SEQUENCE: 88
agaaagctgg gttcctgcgc ttgaaggtct                                   30

<210> SEQ ID NO 89
<211> LENGTH: 32
<212> TYPE: DNA
<213> ORGANISM: Artificial Sequence
<220> FEATURE:
<223> OTHER INFORMATION: PF7 promoter forward primer

<400> SEQUENCE: 89
aaaaagcagg ctaactgaac agggccttac ca                                32

<210> SEQ ID NO 90
<211> LENGTH: 30
<212> TYPE: DNA
<213> ORGANISM: Artificial Sequence
<220> FEATURE:
<223> OTHER INFORMATION: PF7 promoter reverse primer

<400> SEQUENCE: 90
agaaagctgg gtcggcaacg aggtcgatac                                   30

<210> SEQ ID NO 91
<211> LENGTH: 32
<212> TYPE: DNA
<213> ORGANISM: Artificial Sequence
<220> FEATURE:
<223> OTHER INFORMATION: SC1 promoter forward primer

<400> SEQUENCE: 91
aaaaagcagg ctgatcactt gtggcagcca ta                                32

<210> SEQ ID NO 92
<211> LENGTH: 32
<212> TYPE: DNA
<213> ORGANISM: Artificial Sequence
<220> FEATURE:
<223> OTHER INFORMATION: SC1 promoter reverse primer

<400> SEQUENCE: 92
agaaagctgg gtcgctaggg ttttgcgaat tt                                32

<210> SEQ ID NO 93
<211> LENGTH: 32
<212> TYPE: DNA
<213> ORGANISM: Artificial Sequence
<220> FEATURE:
<223> OTHER INFORMATION: SC2 promoter forward primer

<400> SEQUENCE: 93
aaaaagcagg ctttacgtat agccttttcc tt                                32

<210> SEQ ID NO 94
<211> LENGTH: 32
<212> TYPE: DNA
<213> ORGANISM: Artificial Sequence
<220> FEATURE:
<223> OTHER INFORMATION: SC2 promoter reverse primer

<400> SEQUENCE: 94
agaaagctgg gtgacagaat atgctgtgac aa                                32

<210> SEQ ID NO 95
<211> LENGTH: 34
```

```
<212> TYPE: DNA
<213> ORGANISM: Artificial Sequence
<220> FEATURE:
<223> OTHER INFORMATION: SC3 promoter forward primer

<400> SEQUENCE: 95
aaaaagcagg ctaccgatgt agatgaatac ttcc                          34

<210> SEQ ID NO 96
<211> LENGTH: 31
<212> TYPE: DNA
<213> ORGANISM: Artificial Sequence
<220> FEATURE:
<223> OTHER INFORMATION: SC3 promoter reverse primer

<400> SEQUENCE: 96
agaaagctgg gtatccttcc gaaacctgaa c                             31

<210> SEQ ID NO 97
<211> LENGTH: 32
<212> TYPE: DNA
<213> ORGANISM: Artificial Sequence
<220> FEATURE:
<223> OTHER INFORMATION: SC4 promoter forward primer

<400> SEQUENCE: 97
aaaaagcagg ctgctcgtag gacaagcagg aa                            32

<210> SEQ ID NO 98
<211> LENGTH: 32
<212> TYPE: DNA
<213> ORGANISM: Artificial Sequence
<220> FEATURE:
<223> OTHER INFORMATION: SC4 promoter reverse primer

<400> SEQUENCE: 98
agaaagctgg gtcttgcgtg ctcctgatct ct                            32

<210> SEQ ID NO 99
<211> LENGTH: 32
<212> TYPE: DNA
<213> ORGANISM: Artificial Sequence
<220> FEATURE:
<223> OTHER INFORMATION: SC5 promoter forward primer

<400> SEQUENCE: 99
aaaaagcagg cttcctcttg ccccttcctc gg                            32

<210> SEQ ID NO 100
<211> LENGTH: 32
<212> TYPE: DNA
<213> ORGANISM: Artificial Sequence
<220> FEATURE:
<223> OTHER INFORMATION: SC5 promoter reverse primer

<400> SEQUENCE: 100
agaaagctgg gttgtgacgt ggcagtctga ca                            32

<210> SEQ ID NO 101
<211> LENGTH: 32
<212> TYPE: DNA
<213> ORGANISM: Artificial Sequence
<220> FEATURE:
<223> OTHER INFORMATION: SC6 promoter forward primer

<400> SEQUENCE: 101
aaaaagcagg ctgtgcactc aaggtcctat gg                            32
```

<210> SEQ ID NO 102
<211> LENGTH: 32
<212> TYPE: DNA
<213> ORGANISM: Artificial Sequence
<220> FEATURE:
<223> OTHER INFORMATION: SC6 promoter reverse primer

<400> SEQUENCE: 102
agaaagctgg gttggcatac agcactccct ct                                32

<210> SEQ ID NO 103
<211> LENGTH: 32
<212> TYPE: DNA
<213> ORGANISM: Artificial Sequence
<220> FEATURE:
<223> OTHER INFORMATION: SC7 promoter forward primer

<400> SEQUENCE: 103
aaaaagcagg ctgtcgaact caccgtgcac ta                                32

<210> SEQ ID NO 104
<211> LENGTH: 34
<212> TYPE: DNA
<213> ORGANISM: Artificial Sequence
<220> FEATURE:
<223> OTHER INFORMATION: SC7 promoter reverse primer

<400> SEQUENCE: 104
agaaagctgg gttggatgct gctctcttct tctc                              34

<210> SEQ ID NO 105
<211> LENGTH: 33
<212> TYPE: DNA
<213> ORGANISM: Artificial Sequence
<220> FEATURE:
<223> OTHER INFORMATION: SC8 promoter forward primer

<400> SEQUENCE: 105
aaaaagcagg ctaaaaaact tgactgccca aaa                               33

<210> SEQ ID NO 106
<211> LENGTH: 30
<212> TYPE: DNA
<213> ORGANISM: Artificial Sequence
<220> FEATURE:
<223> OTHER INFORMATION: SC8 promoter reverse primer

<400> SEQUENCE: 106
agaaagctgg gtggaaacgg tggtggttct                                   30

<210> SEQ ID NO 107
<211> LENGTH: 29
<212> TYPE: DNA
<213> ORGANISM: Artificial Sequence
<220> FEATURE:
<223> OTHER INFORMATION: attB1 adaptor primer

<400> SEQUENCE: 107
ggggacaagt ttgtacaaaa aagcaggct                                    29

<210> SEQ ID NO 108
<211> LENGTH: 29
<212> TYPE: DNA
<213> ORGANISM: Artificial Sequence
<220> FEATURE:
<223> OTHER INFORMATION: attB2 adaptor primer

```
<400> SEQUENCE: 108
ggggaccact ttgtacaaga aagctgggt                                              29

<210> SEQ ID NO 109
<211> LENGTH: 21
<212> TYPE: DNA
<213> ORGANISM: Artificial Sequence
<220> FEATURE:
<223> OTHER INFORMATION: GFP forward primer

<400> SEQUENCE: 109
cagcacgact tcttcaagtc c                                                      21

<210> SEQ ID NO 110
<211> LENGTH: 21
<212> TYPE: DNA
<213> ORGANISM: Artificial Sequence
<220> FEATURE:
<223> OTHER INFORMATION: GFP reverse primer

<400> SEQUENCE: 110
cttcagctcg atgcggttca c                                                      21
```